US006617281B1

United States Patent
Andree et al.

(10) Patent No.: US 6,617,281 B1
(45) Date of Patent: Sep. 9, 2003

(54) SUBSTITUTED ACYLAMINO PHENYL URACILS

(75) Inventors: Roland Andree, Langenfeld (DE); Mark Wilhelm Drewes, Langenfeld (DE); Dieter Feucht, Monheim (DE); Rolf Pontzen, Leichlingen (DE); Ingo Wetcholowsky, Estancia Marambaia (BR)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/743,066

(22) PCT Filed: Jul. 7, 1999

(86) PCT No.: PCT/EP99/04743

§ 371 (c)(1),
(2), (4) Date: Feb. 20, 2001

(87) PCT Pub. No.: WO00/02867

PCT Pub. Date: Jan. 20, 2000

(30) Foreign Application Priority Data

Jul. 9, 1998 (DE) .......................... 198 30 694

(51) Int. Cl.$^7$ ...................... C07D 403/12; A01N 43/54
(52) U.S. Cl. ...................... 504/243; 544/310; 544/311; 544/312; 544/296
(58) Field of Search ................. 544/296, 310, 544/311, 312; 504/243

(56) References Cited

U.S. PATENT DOCUMENTS

| 5,084,084 A | 1/1992 | Satow et al. ................... 71/92 |
| 5,127,935 A | 7/1992 | Satow et al. ................... 71/92 |
| 5,154,755 A | 10/1992 | Satow et al. ................... 71/92 |
| 5,356,863 A | 10/1994 | Satow et al. ................. 504/243 |
| 5,759,957 A | 6/1998 | Andree et al. ............... 504/243 |
| 5,962,372 A | 10/1999 | Andree et al. ............... 504/243 |
| 6,008,160 A | 12/1999 | Andree et al. ............... 504/243 |
| 6,130,225 A | 10/2000 | Drewes et al. .............. 514/274 |

FOREIGN PATENT DOCUMENTS

| DE | 19 523 640 | 1/1997 |
| EP | 0 563 384 | 10/1993 |
| WO | 96/35679 | 11/1996 |
| WO | 97/01542 | 1/1997 |

*Primary Examiner*—John M. Ford
(74) *Attorney, Agent, or Firm*—Joseph C. Gil; John E. Mrozinski, Jr.; Richard E. L. Henderson

(57) ABSTRACT

The invention relates to new substituted acylaminophenyl-uracils of the general formula (I)

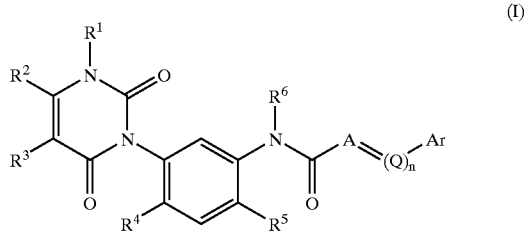

in which n, A, Ar, $Q^1$, $R^1$, $R^2$, $R^3$, $R^4$, $R^5$ and $R^6$ have the meanings given in the description, and to a process for their preparation, and to their use as herbicides.

19 Claims, No Drawings

SUBSTITUTED ACYLAMINO PHENYL URACILS

This application is a 371 National Application of PCT/EP99/04743, filed Jul. 7, 1999.

FIELD OF THE INVENTION

The invention relates to new substituted acylaminophenyl-uracils, to processes for their preparation, and to their use as herbicides.

BACKGROUND OF THE INVENTION

Certain substituted aryluracils have already been disclosed in the (patent) literature (cf. EP-A-408382, U.S. Pat. No. 5,084,084, U.S. Pat. No. 5,127,935, U.S. Pat. No. 5,154,755, EP-A-563384, U.S. Pat. No. 5,356,863, WO-A-95/29168, WO-A-96/35679, WO-A-97/01542, WO-A-97/09319, WO-A-98/06706). However, these compounds have not gained any particular importance to date.

SUMMARY OF THE INVENTION

Novel substituted acylaminophenyl-uracils have the general formula (I)

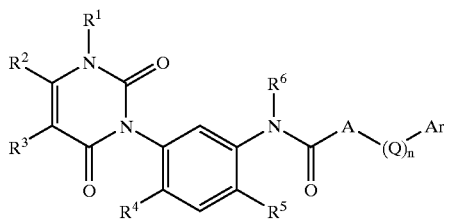

in which:
- n represents the numbers 0 or 1,
- A represents in each case optionally substituted alkanediyl (alkylene) or acycloalkanediyl, or—with the proviso that n then represents 1—also represents a single bond or is attached to Ar via an alkanediyl grouping,
- Ar represents in each case optionally substituted aryl, arylalkyl, heterocyclyl or heterocyclylalkyl,
- Q represents O, S, SO, $SO_2$, NH or N(alkyl),
- $R^1$ represents hydrogen, amino or optionally substituted alkyl,
- $R^2$ represents carboxyl, cyano, carbamoyl, thiocarbamoyl or represents in each case optionally substituted alkyl or alkoxycarbonyl,
- $R^3$ represents hydrogen, halogen or optionally substituted alkyl,
- $R^4$ represents hydrogen, cyano, carbamoyl, thiocarbamoyl or halogen,
- $R^5$ represents cyano, carbamoyl, thiocarbamoyl, halogen, or represents in each case optionally substituted alkyl or alkoxy, and
- $R^6$ represents hydrogen or represents in each case optionally substituted alkyl, alkylcarbonyl, alkoxycarbonyl, alkylsulphonyl, alkenyl, alkenylcarbonyl, alkenylsulphonyl, alkinyl, cycloalkylcarbonyl, cycloalkylsulphonyl, arylcarbonyl, arylsulphonyl, arylalkylcarbonyl, arylalkylsulphonyl, heterocyclylcarbonyl or heterocyclylsulphonyl.

DETAILED DESCRIPTION

In the definitions, the hydrocarbon chains, such as alkyl or alkanediyl—also in connection with heteroatoms such as in alkoxy—are in each case straight-chain or branched.

In as far as the compounds of the general formula (I) according to the invention contain asymmetrically substituted carbon atoms, the invention relates in each case to the R enantiomers and the S enantiomers and to any mixtures of these enantiomers, in particular the racemates.

A preferably represents in each case optionally halogen-substituted alkanediyl (alkylene) having 1 to 6 carbon atoms or cycloalkanediyl having 3 to 6 carbon atoms or—in the case that n then represents 1—also represents a single bond or is attached to Ar via an alkanediyl grouping having 1 to 3 carbon atoms;

Ar preferably represents in each case optionally substituted aryl or arylalkyl having in each case 6 or 10 carbon atoms in the aryl group and optionally 1 to 4 carbon atoms in the alkyl moiety, or represents in each case optionally substituted heterocyclyl or heterocylylalkyl having in each case 1 to 5 carbon atoms and at least one heteroatom (up to 4 nitrogen atoms and/or optionally 1 or 2 oxygen or sulphur atoms), where the substituents that are possible in each case are preferably selected from the following list:
nitro, cyano, carboxyl, carbamoyl, thiocarbamoyl, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-lalogenoalkylsulphonyl, $C_1$–$C_4$-alkylamino, di-($C_1$–$C_4$-alkyl)-amino, $C_1$–$C_4$-alkyl-carbonyl, $C_1$–$C_4$-alkoxycarbonyl, $C_1$–$C_4$-alkylamino-carbonyl, di-($C_1$–$C_4$-alkyl)-amino-carbonyl, di-($C_1$–$C_4$-alkyl)-amino-sulphonyl, Q preferably represents O (oxygen), S (sulphur), SO, $SO_2$, NH or N($C_1$–$C_4$-alkyl), $R^1$ preferably represents hydrogen, amino or optionally cyano-, carboxyl-, halogen-, $C_1$–$C_4$-alkoxy-or $C_1$–$C_4$-alkoxycarbonyl-substituted alkyl having 1 to 6 carbon atoms, $R^2$ preferably represents carboxyl, cyano, carbamoyl, thiocarbamoyl or represents in each case optionally cyano-, halogen- or $C_1$–$C_4$-alkoxy-substituted alkyl or alkoxycarbonyl having in each case 1 to 6 carbon atoms in the alkyl groups, $R^3$ preferably represents hydrogen, halogen or optionally halogen-substituted alkyl having 1 to 6 carbon atoms, $R^4$ preferably represents hydrogen, cyano, carbamoyl, thiocarbamoyl, fluorine or chlorine, $R^5$ preferably represents cyano, carbamoyl, thiocarbamoyl, halogen, or represents in each case optionally halogen-substituted alkyl or alkoxy having in each case 1 to 4 carbon atoms, and $R^6$ preferably represents hydrogen, represents in each case optionally cyano-, halogen- or $C_1$–$C_4$-alkoxy-substituted alkyl, alkylcarbonyl or alkoxycarbonyl having in each case 1 to 6 carbon atoms in the alkyl groups, represents optionally halogen-substituted alkylsulphonyl having 1 to 6 carbon atoms, represents in each case optionally halogen-substituted alkenyl, alkenylcarbonyl, alkenylsulphonyl or alkinyl having in each case up to 6 carbon atoms, represents in each case optionally halogen-substituted cycloalkylcarbonyl or cycloalkylsulphonyl having in each case 3 to 6 carbon atoms in the cycloalkyl groups, represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$- halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl, $C_1$–$C_4$-alkylcarbonyl-, $C_1$–$C_4$-alkoxy-carbonyl- or di-($C_1$–$C_4$-alkyl-amino)-sulphonyl-substituted arylcarbonyl, arylsulphonyl, arylalkylcarbonyl or arylalkylsulphonyl having in each case 6 or 10 carbon atoms in the aryl groups and optionally 1 to 4 carbon atoms in the alkyl moiety, or represents in each case optionally nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkylcarbonyl-, $C_1$–$C_4$-alkoxy-carbonyl- or di-($C_1$–$C_4$-alkyl-amino)-sulphonyl-substituted heterocyclylcarbonyl or heterocyclylsulphonyl having 1 to 5 carbon atoms and 1 to 4 nitrogen atoms and/or 1 or 2 oxygen or sulphur atoms;

A particularly preferably represents in each case optionally fluorine- and/or chlorine-substituted methylene, ethane-1,1-diyl(ethylidene), ethane-1,2-diyl (dimethylene), propane-1,1-diyl(propylidene), propane-1,2-diyl or propane-1,3-diyl(trimethylene), cyclopropane-1,1-diyl, cyclopropane-1,2-diyl, cyclobutane-1,1-diyl, cyclopentane-1,1-diyl or cyclohexane-1,1-diyl, or—in the case that n then represents 1—also represents a single bond, or is attached to Ar via a 1,2-ethanediyl(dimethylene) grouping;

Ar particularly preferably represents in each case optionally substituted phenyl, naphthyl, benzyl, 1-phenyl-ethyl, 2-phenyl-ethyl, 1-phenyl-propyl, 2-phenyl-propyl or 3-phenyl-propyl, or represents in each case optionally substituted heterocyclyl or heterocyclylalkyl selected from the group consisting of oxiranyl, oxiranylmethyl, oxetanyl, oxetanylmethyl, furyl, furylmethyl, tetrahydrofuryl, tetrahydrofurylmethyl, thienyl, thienylmethyl, tetrahydrothienyl, tetrahydrothienylmethyl, benzofuryl, benzofurylmethyl, dihydrobenzofuryl, dihydrobenzofurylmethyl, benzothienyl, benzothienylmethyl, pyrrolyl, pyrrolylmethyl, pyrazolyl, pyrazolylmethyl, pyranyl, pyranylmethyl, benzopyranyl, benzopyranylmethyl, dihydrobenzopyranyl, dihydrobenzopyranylmethyl, tetrahydrobenzopyranyl, tetrahydrobenzopyranylmethyl, pyridinyl, pyridinylmethyl, pyrimidinyl, pyrimidinylmethyl, where the substituents that arc possible in each case are preferably selected from the following list:

nitro, cyano, carboxyl, carbamoyl, thiocarbamoyl, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, methylthio, ethylthio, n- or i-propylthio, n-, i-, s- or t-butylthio, difluoromethylthio, trifluoromethylthio, methylsulphinyl, ethylsulphfinyl, n- or i-propylsulphinyl, trifluoromethylsulphinyl, methylsulphonyl, ethylsulphonyl, n- or i-propylsulphonyl, trifluoromethylsulphonyl, methylamino, ethylamino, n- or i-propylamino, n-, i-, s- or t-butylamino, dimethylamino, diethyl-amino, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, dimethylaminocarbonyl, diethylaminocarbonyl, dimethylaminosulphonyl, diethylaminosulphonyl, Q particularly preferably represents O (oxygen), S (sulphur), SO, $SO_2$, NH or N(methyl), $R^1$ particularly preferably represents hydrogen, amino or in each case optionally cyano-, fluorine-, chlorine-, methoxy- or ethoxy-substituted methyl or ethyl, $R^2$ particularly preferably represents carboxyl, cyano, carbamoyl, thiocarbamoyl or represents in each case optionally cyano-, fluorine-, chlorine-, methoxy- or ethoxy-substituted methyl, ethyl, n- or i-propyl, methoxycarbonyl or ethoxycarbonyl, $R^3$ particularly preferably represents hydrogen, fluorine, chlorine, bromine or in each case optionally fluorine- or chlorine-substituted methyl, ethyl, n- or i-propyl, $R^4$ particularly preferably represents hydrogen, fluorine or chlorine, $R^5$ particularly preferably represents cyano, carbamoyl, thiocarbamoyl, fluorine, chlorine, bromine, or represents in each case optionally fluorine- and/or chlorine-substituted methyl, ethyl, n- or i-propyl, methoxy, ethoxy, n- or i-propoxy.

$R^6$ particularly preferably represents hydrogen, represents in each case optionally cyano-, fluorine-, chlorine-, methoxy- or ethoxy-substituted methyl, ethyl, n- or i-propyl, n-, i-, s- or t-butyl, acetyl, propionyl, n- or i-butyroyl, n-, i- or sec-valeroyl, pivaloyl, methoxycarbonyl, ethoxycarbonyl, n- or i-propoxycarbonyl, represents in each case optionally fluorine- and/or chlorine-substituted methylsulphonyl, ethylsulphonyl, n- or i-propylsulphonyl, n-, i-, s- or t-butylsulphonyl, represents in each case optionally fluorine-, chlorine- and/or bromine-substituted ethenyl, propenyl, butenyl, ethenylcarbonyl, propenylcarbonyl, butenylcarbonyl, ethinyl, propinyl or butinyl, represents in each case optionally fluorine-, chlorine- and/or bromine-substituted cyclopropylcarbonyl, cyclopropylmethylcarbonyl, cyclobutylcarbonyl, cyclobutylmethylcarbonyl, cyclopentylcarbonyl, cyclopentylmethylcarbonyl, cyclohexylcarbonyl, cyclohexylmethylcarbonyl, cyclopropylsulphonyl, cyclopropylmethylsulphonyl, cyclobutylsulphonyl, cyclobutylmethylsulphonyl, cyclopentylsulphonyl, cyclopentylmethylsulphonyl, cyclohexylsulphonyl or cyclohexylmethylsulphonyl, represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, acetyl-, propionyl-, n- or i-butyroyl-, methoxycarbonyl-, ethoxycarbonyl-, n- or i-propoxycarbonyl-, dimethylaminosulphonyl- or diethylamino-sulphonyl-substituted benzoyl, phenylsulphonyl, phenylacetyl, phenylpropionyl, benzylsulphonyl or phenylethylsulphonyl, or represents in each case optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, acetyl-, propionyl-, n- or i-butyroyl-, methoxycarbonyl-, ethoxycarbonyl-, n- or i-propoxy-carbonyl-, dimethylaminosulphonyl- or diethyl-aminosulphonyl-substituted heterocyclylcarbonyl or heterocyclylsulphonyl selected from the group consisting of furylcarbonyl, furylsulphonyl, thienylcarbonyl, thienylsulphonyl, pyrazolylcarbonyl, pyrazolylsulphonyl, pyridinylcarbonyl, pyridinylsulphonyl, quinolinylcarbonyl, quinolinylsuiphonyl, pyrimidinylcarbonyl, pyrimidinylsulphonyl;

A very particularly preferably represents methylene, ethane-1,1-diyl(ethylidene) or ethane-1,2-diyl (dimethylene), Ar very particularly preferably represents in each case optionally substituted phenyl, naphthyl or benzyl,
  where the substituents that are possible in each case are selected in particular from the following list:
    nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy, trifluoromethoxy, methylthio, ethylthio, n- or i-propylthio, difluoromethylthio, trifluoromethylthio, methylsulphinyl, ethylsulphinyl, n- or i-propylsulphinyl, trifluoromethylsulphinyl, methylsulphonyl, ethylsulphonyl, n- or i-propylsulphonyl, trifluoromethylsulphonyl, methoxycarbonyl, ethoxycarbonyl, n- or i-propoxycarbonyl, Q very particularly preferably represents O (oxygen), $R^1$ very particularly preferably represents hydrogen, amino or methyl, $R^2$ very particularly preferably represents trifluoromethyl, $R^3$ very particularly preferably represents hydrogen, chlorine or methyl, $R^4$ very particularly preferably represents hydrogen, fluorine or chlorine, $R^5$ very particularly preferably represents cyano, carbamoyl, thiocarbamoyl, chlorine or bromine, $R^6$ very particularly preferably represents hydrogen, represents in each case optionally fluorine- and/or chlorine-substituted methylsulphonyl, ethylsulphonyl, n- or i-propylsulphonyl, n-, i- s- or t-butylsulphonyl, or represents optionally fluorine- and/or chlorine-substituted cyclopropylsulphonyl;

Ar most preferably represents in each case optionally substituted phenyl or naphthyl,
  where the substituents that are possible in each case are selected in particular from the following list:
    nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy, trifluoromethoxy, methylthio, ethylthio, n- or i-propylthio, difluoromethylthio, trifluoromethylthio, methylsulphinyl, ethylsulphinyl, n- or i-propylsulphinyl, trifluoromethylsulphinyl, methylsulphonyl, ethylsulphonyl, n- or i-propylsulphonyl, trifluoromethylsulphonyl, methoxycarbonyl, ethoxycarbonyl, n- or i-propoxycarbonyl.

The abovementioned general or preferred radical definitions apply both to the end products of the formula (I) and also correspondingly to the starting materials or intermediates required in each case for the preparation. These radical definitions can be combined with each other as desired, i.e. including combinations between the given preferred ranges.

Preferred according to the invention are those compounds of the formula (I) in which there exists a combination of the meanings mentioned above as being preferred.

Especially preferred according to the invention are those compounds of the formula (I) in which there exists a combination of the meanings mentioned above as being especially preferred.

Very especially preferred according to the invention are those compounds of the formula (I) in which there exists a combination of the meanings mentioned above as being very especially preferred.

Most preferred according to the invention are those compounds of the formula (I) in which there exists a combination of the meanings mentioned above as being most preferred.

Examples of the compounds of the general formula (I) according to the invention are given in the groups which follow.

Group 1

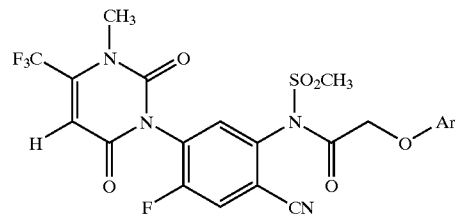

Ar here has the meanings given in the list below:

2-cyano-phenyl, 3-cyano-phenyl, 4-cyano-phenyl, 2-fluoro-phenyl, 3-fluoro-phenyl, 4-fluoro-phenyl, 2,3-difluoro-phenyl, 2,4-difluoro-phenyl, 2,5-difluoro-phenyl, 2,6-difluoro-phenyl, 3,4-difluoro-phenyl, 3,5-difluoro-phenyl, 2-chloro-phenyl, 3-chloro-phenyl, 4-chloro-phenyl, 2,3-dichloro-phenyl, 2,4-dichloro-phenyl, 2,5-dichloro-phenyl, 2,6-dichloro-phenyl, 3,4-dichloro-phenyl, 3,5-dichloro-phenyl, 2-bromo-phenyl, 3-bromo-phenyl, 4-bromo-phenyl, 2-methyl-phenyl, 3-methyl-phenyl, 4-methyl-phenyl, 2,3-dimethyl-phenyl, 2,4-dimethyl-phenyl, 2,5-dimethyl-phenyl, 2,6-dimethyl-phenyl, 3,4-dimethyl-phenyl, 3,5-dimethyl-phenyl, 2-trifluoromethyl-phenyl, 3-trifluoromethyl-phenyl, 4-trifluoromethyl-phenyl, 2-methoxy-phenyl, 3-methoxy-phenyl, 4-methoxy-phenyl, 2,4-dimethoxy-phenyl, 2,5-dimethoxy-phenyl, 2,6-dimethoxy-phenyl, 3,4-dimethoxy-phenyl, 2-difluoromethoxy-phenyl, 4-difluoromethoxy-phenyl, 2-trifluoromethoxy-phenyl, 4-trifluoromethoxy-phenyl, 2-chloro-4-methyl-phenyl, 4-chloro-2-methyl-phenyl, 2-fluoro-4-chloro-phenyl, 2-chloro-4-fluoro-phenyl, 2-chloro-4-bromo-phenyl, 2-bromo-4-chloro-phenyl, 2-fluoro-4-bromo-phenyl, 2-bromo-4-fluoro-phenyl, 4-fluoro-2-methyl-phenyl, 4-bromo-2-methyl-phenyl.

Group 2

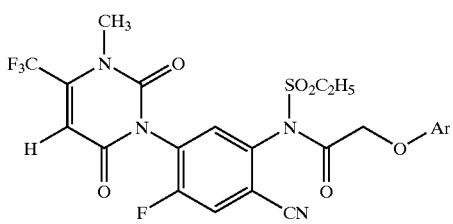

Ar here has the meanings given above under Group 1

Group 3

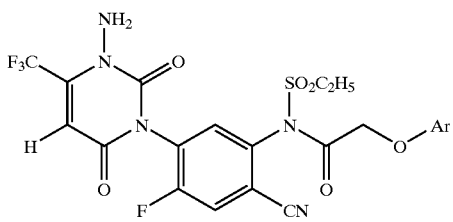

Ar here has the meanings given above under Group 1

Group 4

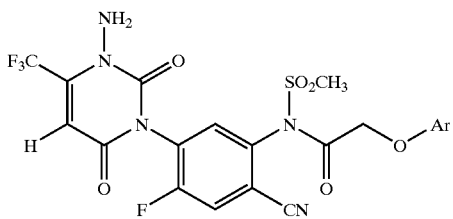

Ar here has the meanings given above under Group 1

Group 5

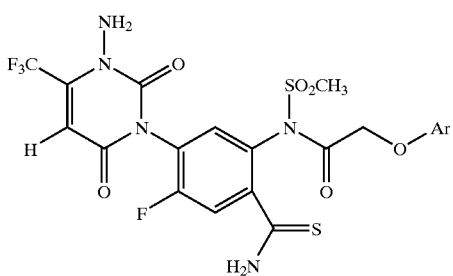

Ar here has the meanings given above under Group 1

Group 6

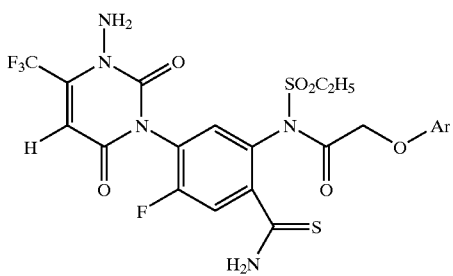

Ar here has the meanings given above under Group 1

Group 7

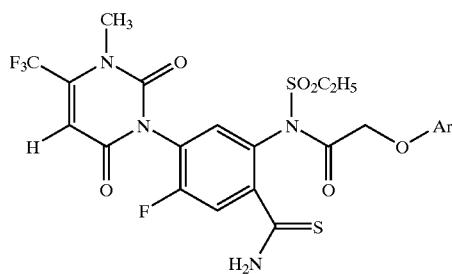

Ar here has the meanings given above under Group 1

Group 8

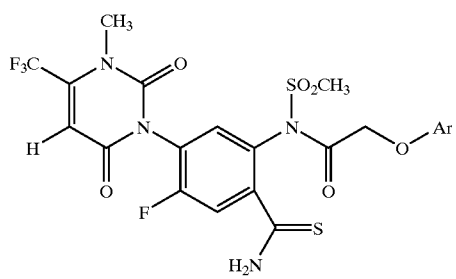

Ar here has the meanings given above under Group 1

Group 9

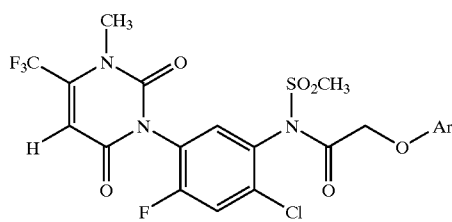

Ar here has the meanings given above under Group 1

Group 10

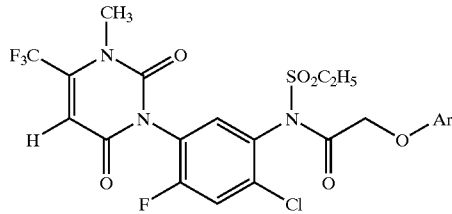

Ar here has the meanings given above under Group 1

Group 11

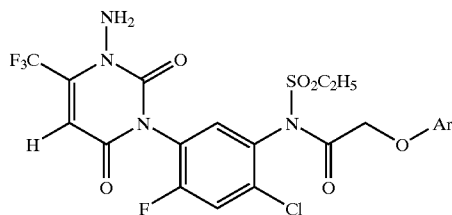

Ar here has the meanings given above under Group 1

Group 12

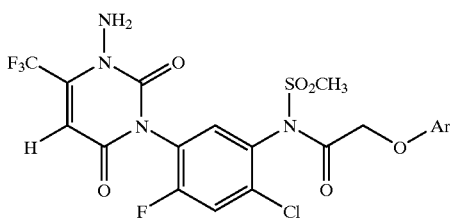

Ar here has the meanings given above under Group 1

Group 13

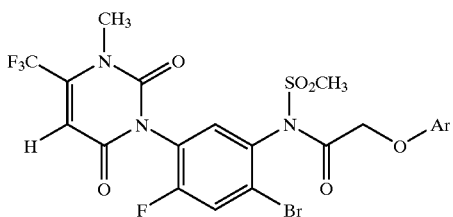

Ar here has the meanings given above under Group 1

Group 14

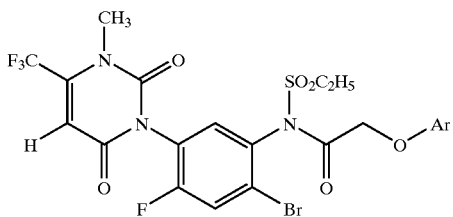

Ar here has the meanings given above under Group 1

Group 15

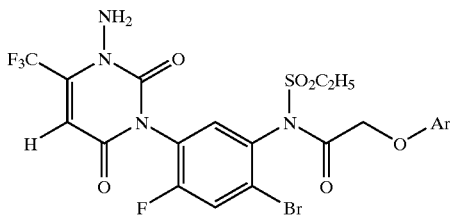

Ar here has the meanings given above under Group 1

Group 16

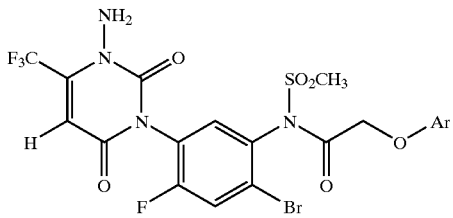

Ar here has the meanings given above under Group 1

The novel substituted acylaminophenyl-uracils of the general formula (I) have interesting biological properties. In particular, they have strong herbicidal activity.

The novel substituted acylaminophenyl-uracils of the general formula (I) are obtained when aminophenyl-uracils of the general formula (II)

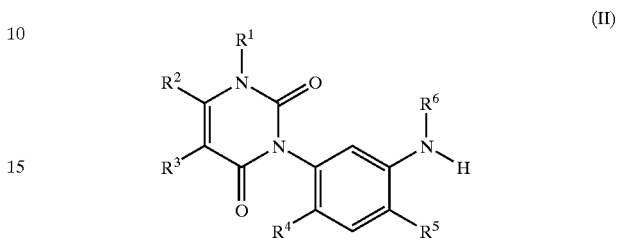

(II)

in which
$R^1$, $R^2$, $R^3$, $R^4$, $R^5$ and $R^6$ are each as defined above
are reacted with acylating agents of the general formula (III)

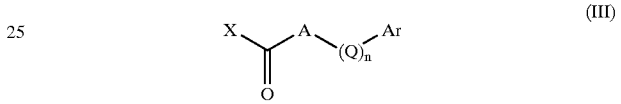

(III)

in which
n, A, Ar and Q are each as defined above and
X represents halogen,
if appropriate in the presence of a reaction auxiliary and if appropriate in the presence of a diluent,
and, if appropriate, electrophilic or nucleophilic reactions or oxidations or reductions within the scope of the definition of the substituents are subsequently carried out in a customary manner.

The compounds of the general formula (I) can be converted by customary methods into other compounds of the general formula (I) according to the above definition, for example by amination or alkylation (for example $R^1$: H→$NH_2$, $CH_3$), reaction with dicyanogen or hydrogen sulphide (for example $R^5$: Br→CN, CN→$CSNH_2$, cf. the Preparation Examples.

Using, for example, 1-(2,4-dichloro-5-methylsulphonylamino-phenyl)-4-difluoro-methyl-3,6-dihydro-2,6-dioxo-1(2H)-pyrimidine and (4-chloro-2-methyl-phenoxy)-acetyl chloride as starting materials, the course of the reaction of the process according to the invention can be illustrated by the following equation:

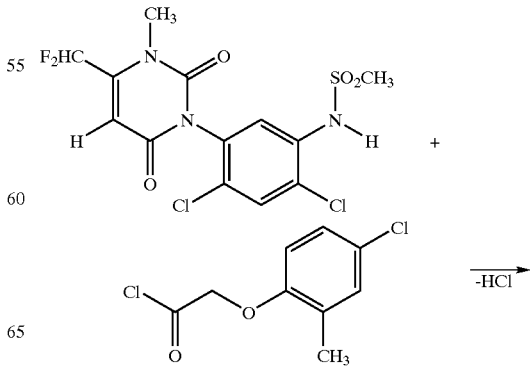

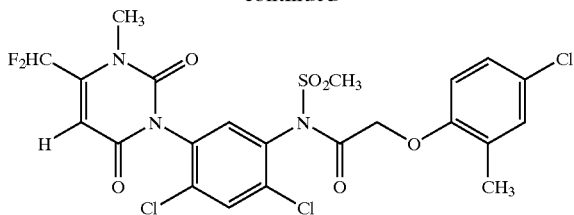

Formula (II) provides a general definition of the aminophenyluracils to be used as starting materials in the process according to the invention for the preparation of compounds of the formula (I). In formula (II), $R^1$, $R^2$, $R^3$, $R^4$, $R^5$ and $R^6$ have, preferably, those meanings which have already been mentioned above in connection with the description of the compounds of the formula (I) according to the invention as being preferred, especially preferred or very especially preferred for $R^1$, $R^2$, $R^3$, $R^4$, $R^5$ and $R^6$.

The starting materials of the general formula (II) are known and/or can be prepared by processes known per se (cf. EP-A-408382, EP-A-648749, WO-A-97/01542).

Formula (III) provides a general definition of the acylating agents also to be used as starting materials in the process according to the invention. In formula (III), n, A, Ar and Q each preferably have those meanings which have already been mentioned above in connection with the description of the compounds of the formula (I) according to the invention as being preferred, particularly preferred, very particularly preferred or most preferred for n, A, Ar and Q; X preferably represents fluorine, chlorine or bromine, in particular chlorine.

The starting materials of the general formula (III) are known chemicals for synthesis.

The process according to the invention for the preparation of the compounds of the general formula (I) is preferably carried out using a reaction auxiliary. Reaction auxiliaries which are suitable for the process according to the invention are, in general, the customary inorganic or organic bases or acid acceptors. These preferably include alkali metal or alkaline earth metal acetates, amides, carbonates, bicarbonates, hydrides, hydroxides or alkoxides, such as, for example, sodium acetate, potassium acetate or calcium acetate, lithium amide, sodium amide, potassium amide or calcium amide, sodium carbonate, potassium carbonate or calcium carbonate, sodium bicarbonate, potassium bicarbonate or calcium bicarbonate, lithium hydride, sodium hydride, potassium hydride or calcium hydride, lithium hydroxide, sodium hydroxide, potassium hydroxide or calcium hydroxide, sodium methoxide, ethoxide, n- or i-propoxide, n-, i-, s- or t-butoxide, or potassium methoxide, ethoxide, n- or i-propoxide, n-, i-, s- or t-butoxide; furthermore also basic organic nitrogen compounds, such as, for example, trimethylamine, triethylamine, tripropylamine, tributylamine, ethyl-diisopropylamine, N,N-dimethyl-cyclo-hexylamine, dicyclohexylamine, ethyl-dicyclohexylamine, N,N-dimethyl-aniline, N,N-dimethyl-benzylamine, pyridine, 2-methyl-, 3-methyl-, 4-methyl-, 2,4-dimethyl-, 2,6-dimethyl-, 3,4-dimethyl- and 3,5-dimethyl-pyridine, 5-ethyl-2-methyl-pyridine, 4-dimethylamino-pyridine, N-methyl-piperidine, 1,4-diazabicyclo[2.2.2]octane (DABCO), 1,5-diazabicyclo[4.3.0]-non-5-ene (DBN), or 1,8-diazabicyclo[5.4.0]-undec-7-ene (DBU).

The process according to the invention for preparing the compounds of the general formula (I) is preferably carried out using a diluent. Suitable diluents for carrying out the process according to the invention are, in particular, inert organic solvents. These preferably include aliphatic, alicyclic or aromatic, optionally halogenated hydrocarbons, such as, for example, benzine, benzene, toluene, xylene, chlorobenzene, dichlorobenzene, petroleum ether, hexane, cyclohexane, dichloromethane, chloroform, carbon tetrachloride; ethers, such as diethyl ether, diisopropyl ether, dioxane, tetrahydrofuran or ethylene glycol dimethyl ether or ethylene glycol diethyl ether; ketones, such as acetone, butanone or methyl-isobutyl ketone; nitriles, such as acetonitrile, propionitrile or butyronitrile; amides, such as N,N-dimethylformamide, N,N-dimethylacetamide, N-methylformanilide, N-methyl-pyrrolidone or hexamethylphosphoric triamide; esters, such as methyl acetate or ethyl acetate, sulphoxides, such as dimethyl sulphoxide, alcohols, such as methanol, ethanol, n- or i-propanol, ethylene glycol monomethyl ether, ethylene glycol monoethyl ether, diethylene glycol monomethyl ether, diethylene glycol monoethyl ether, mixtures thereof with water, or pure water.

When carrying out the process according to the invention, the reaction temperatures can be varied within a substantial range. In general, the process is carried out at temperatures between 0° C. and 150° C., preferably between 10° C. and 120° C.

The process according to the invention is generally carried out under atmospheric pressure. However, it is also possible to carry out the processes according to the invention under elevated or reduced pressure, in general between 0.1 bar and 10 bar.

To carry out the process according to the invention, the starting materials are generally employed in approximately equimolar amounts. However, it is also possible to use one of the components in a larger excess. In general, the reaction is carried out in a suitable diluent in the presence of a reaction auxiliary, and the reaction mixture is generally stirred for several hours at the temperature required. Working-up is by.customary methods (cf. the preparation examples).

The active compounds according to the invention can be used as defoliants, desiccants, haulm killers and, especially, as weedkillers. By weeds, in the broadest sense, there are to be understood all plants which grow in locations where they are undesired. Whether the substances according to the invention act as total or selective herbicides depends essentially on the amount used.

The active compounds according to the invention can be used, for example, in connection with the following plants:

Dicotyledonous weeds of the genera: Sinapis, Lepidium, Galium, Stellaria, Matricaria, Anthemis, Galinsoga, Chenopodium, Urtica, Senecio, Amaranthus, Portulaca, Xanthium, Convolvulus, Ipomoea, Polygonum, Sesbania, Ambrosia, Cirsiun, Carduus, Sonchus, Solanum, Rorippa, Rotala, Lindernia, Lamium, Veronica, Abutilon, Emex, Datura, Viola, Galeopsis, Papaver, Centaurea, Trifolium, Ranunculus and Taraxacum.

Dicotyledonous crops of the genera: Gossypium, Glycine, Beta, Daucus, Phaseolus, Pisum, Solanum, Linum, Ipomoea, Vicia, Nicotiana, Lycopersicon, Arachis, Brassica, Lactuca, Cucumis and Cucurbita.

Monocotyledonous weeds of the genera: Echinochloa, Setaria, Panicum, Digitaria, Phleum, Poa, Festuca, Eleusine, Brachiaria, Lolium, Bromus, Avena, Cyperus, Sorghum, Agropyron, Cynodon, Monochoria, Fimbristylis, Sagittaria, Eleocharis, Scirpus, Paspalum, Ischaemum, Sphenoclea, Dactyloctenium, Agrostis, Alopecurus and Apera.

Monocotyledonous crops of the genera: Oryza, Zea, Triticum, Hordeum, Avena, Secale, Sorghum, Panicum, Saccharum, Ananas, Asparagus and Allium.

However, the use of the active compounds according to the invention is in no way restricted to these genera, but also extends in the same manner to other plants.

Depending on the concentration, the compounds are suitable for total weed control, for example on industrial terrain and rail tracks, and on paths and areas with or without tree stands. Equally, the compounds can be employed for controlling weeds in perennial crops, for example forests, ornamental tree plantings, orchards, vineyards, citrus groves, nut orchards, banana plantations, coffee plantations, tea plantations, rubber plantations, oil palm plantations, cocoa plantations, soft fruit plantings and hopfields, in lawns, turf and pastures, and for selective weed control in annual crops.

The compounds of the formula (I) according to the invention are suitable for controlling monocotyledonous and dicotyledonous weeds both by the pre-emergence and by the post-emergence method. They have high herbicidal activity and a broad activity spectrum when used on the soil and on above-ground parts of plants.

The active compounds can be converted into the customary formulations, such as solutions, emulsions, wettable powders, suspensions, powders, dusts, pastes, soluble powders, granules, suspoemulsion concentrates, natural and synthetic materials impregnated with active compound, and microencapsulations in polymeric substances.

These formulations are produced in a known manner, for example by mixing the active compounds with extenders, that is liquid solvents and/or solid carriers, optionally with the use of surfactants, that is emulsifiers and/or dispersants and/or foam-formers.

If water is used as an extender, organic solvents can, for example, also be used as auxiliary solvents. Liquid solvents which are mainly suitable are: aromatics such as xylene, toluene, or alkylnaphthalenes, chlorinated aromatics and chlorinated aliphatic hydrocarbons such as chlorobenzenes, chloroethylenes or methylene chloride, aliphatic hydrocarbons such as cyclohexane or paraffins, for example petroleum fractions, mineral and vegetable oils, alcohols such as butanol or glycol as well as their ethers and esters, ketones such as acetone, methyl ethyl ketone, methyl isobutyl ketone or cyclohexanone, strongly polar solvents such as dimethylformamide and dimethyl sulphoxide, and water.

Suitable solid carriers are: for example ammonium salts and ground natural minerals such as kaolins, clays, talc, chalk, quartz, attapulgite, montmorillonite or diatomaceous earth, and ground synthetic minerals such as highly disperse silica, alumina and silicates; suitable solid carriers for granules are: for example crushed and fractionated natural rocks such as calcite, marble, pumice, sepiolite and dolomite, or else synthetic granules of inorganic and organic meals, and granules of organic material such as sawdust, coconut shells, maize cobs and tobacco stalks; suitable emulsifiers and/or foam formers are: for example non-ionic and anionic emulsifiers, such as polyoxyethylene fatty acid esters, polyoxyethylene fatty alcohol ethers, for example alkylaryl polyglycol ethers, alkylsulplhonates, alkyl sulphates, arylsulphonates and protein hydrolyzates; suitable dispersants are: for example lignin-sulphite waste liquors and methylcellulose.

Adhesives such as carboxymethylcellulose and natural and synthetic polymers in the form of powders, granules or latexes such as gum arabic, polyvinyl alcohol and polyvinyl acetate, or else natural phospholipids such as cephalins and lecithins, and synthetic phospholipids can be used in the formulations. Further additives can be mineral and vegetable oils.

It is possible to use colorants such as inorganic pigments, for example iron oxide, titanium oxide and Prussian Blue, and organic dyestuffs such as alizarin dyestuffs, azo dyestuffs and metal phthalocyanine dyestuffs, and trace nutrients such as salts of iron, manganese, boron, copper, cobalt, molybdenum and zinc.

The formulations generally comprise between 0.1 and 95 per cent by weight of active compound, preferably between 0.5 and 90%.

For controlling weeds, the active compounds according to the invention, as such or in the form of their formulations, can also be used as mixtures with known herbicides, ready-mixes or tank mixes being possible.

Possible components for the mixtures are known herbicides, such as, for example, acetochlor, acifluorfen(-sodium), aclonifen, alachlor, alloxydim(-sodium), ametryne, amidochlor, amidosulfuron, anilofos, asulam, atrazine, azafenidin, azimsulfuron, benazolin(-ethyl), benfuresate, bensulfuron(-methyl), bentazone, benzofenap, benzoylprop (-ethyl), bialaphos, bifenox, bispyribac(-sodium), bromobutide, bromofenoxim, bromnoxynil, butachlor, butroxydim, butylate, cafenstrole, caloxydim, carbetamde, carfentrazone(-ethyl), chlomethoxyfen, chloramben, chloridazon, chlorimuron(-ethyl), chlornitrofen, chlorsulfuron, chlortoluron, cinidon(-ethyl), cinmethylin, cinosulfuron, clethodim, clodinafop(-propargyl), clomazone, clomeprop, clopyralid, clopyrasulfuron(-methyl), cloransulam(-methyl), cumyluron, cyanazine, cybutryne, cycloate, cyclosulfamuron, cycloxydim, cyhalofop(-butyl), 2,4-D, 2,4-DB, 2,4-DP, desmedipham, di-allate, dicamba, diclofop(-methyl), diclosulam, diethatyl (-ethyl), difenzoquat, diflufenican, diflufenzopyr, dimefuron, dimepiperate, dimethachlor, dimethametryn, dimethenamid, dimexyflam, dinitramine, diphenamid, diquat, dithiopyr, diuron, dymrone, epoprodan, EPTC, esprocarb, ethalfluralin, ethametsulfuron(-methyl), ethofumesate, ethoxyfen, ethoxysulfuron, etobenzanid, fenoxaprop(-P-ethyl), flamprop(-isopropyl), flamprop(-isopropyl-L), flamprop(-methyl), flazasulfuron, fluazifop(-P-butyl), fluazolate, flucarbazone, flufenacet, flumetsulam, flumiclorac(-pentyl), flumioxazin, flumipropyn, flumetsulam, fluometuron, fluorochloridone, fluoroglycofen (-ethyl), flupoxam, flupropacil, flurpyrsulfuron(-methyl, -sodium), flurenol(-butyl), fluridone, fluroxypyr(-meptyl), flurprimidol, flurtamone, fluthiacet(-methyl), fluthiamide, fomesafen, glufosinate(-ammonium), glyphosate(-isopropylammonium), halosafen, haloxyfop(-ethoxyethyl), haloxyfop(-P-methyl), hexazinone, imazamethabenz-(-methyl), imazamethapyr, imazamox, imazapic, imazapyr, imazaquin, imazethapyr, imazosulfuron, iodosulfuron, ioxynil, isopropalin, isoproturon, isouron, isoxaben, isoxachlortole, isoxaflutole, isoxapyrifop, lactofen, lenacil, linuron, MCPA, MCPP, mefenacet, mesotrione, metamitron, metazachlor, metha-benzthiazuron, metobenzuron, metobromuron, (alpha-)metolachlor, metosulam, metoxuron, metribuzin, metsulfuron(-methyl), molinate, monolinuron, naproanilide, napropamide, neburon, nicosulfuron, norflurazon, orbencarb, oryzalin, oxadiargyl, oxadiazon, oxasulfuron, oxaziclomefone, oxyfluorfen, paraquat, pelargonic acid, pendimethalin, pentoxazone, phenmedipham, piperophos, pretilachlor, primisulfuron(-methyl), prometryn, propachlor, propanil, propaquizafop, propisochlor, propyzanide, prosulfocarb, prosulfuron, pyraflufen(-ethyl), pyrazolate, pyrazosulfuron(-ethyl), pyrazoxyfen, pyribenzoxim, pyributicarb, pyridate, pyriminobac(-methyl), pyrithiobac(-sodium), quinchlorac, quinmerac, quinoclamine, quizalofop(-P-ethyl), quizalofop (-P-tefuryl), rimsulfuron, sethoxydim, simazine, simetryn, sulcotrione, sulfentrazone, sulfometuron(-methyl), sulfosate, sulfosulfuron, tebutam, tebuthiuron, tepraloxydim, terbuthylazine, terbutryn, thenylchlor, thiafluamide, thiazopyr, thidiazimin, thifensulfuron(-methyl), thiobencarb, tiocarbazil, tralkoxydim, tri-allate, triasulfuron, tribenuron(-methyl), triclopyr, tridiphane, trifluralin and triflusulfuron.

Mixtures with other known active compounds such as fungicides, insecticides, acaricides, nematicides, bird repellants, plant nutrients and soil conditioners, are also possible.

The active compounds can be used as such, in the form of their formulations or in the use forms prepared therefrom by further dilution, such as ready-to-use solutions, suspensions, emulsions, powders, pastes and granules. They are used in the customary manner, for example by pouring, spraying, atomizing or spreading.

The active compounds according to the invention can be applied either before or after emergence of the plants. They can also be incorporated into the soil before sowing.

The amount of active compound used can vary within a substantial range. It depends essentially on the nature of the desired effect. In general, the application rates are between 1 and 10 kg of active compound per hectare of soil surface, preferably between 5 and 5 kg per ha.

The preparation and use of the active compounds according to the invention can be seen from the examples which follow.

PREPARATION EXAMPLES

Example 1

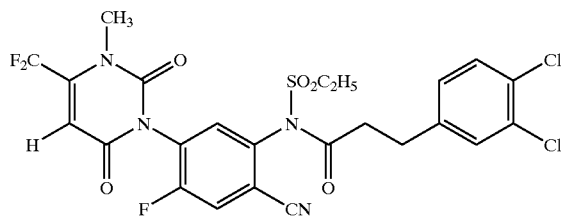

At room temperature (approximately 20° C.), a mixture of 2.1 g (5 mmol) of 1-(4-cyano-5-ethylsulphonylamino-2-fluorophenyl)-3-methyl-4-trifluoromethyl-3,6-dihydro-2,6-dioxo-1(2H)-pyrimidine, 1.42 g (5 mmol) of 3-(3,4-dichloro-phenyl)-propionyl chloride, 0.63 g of triethylamine and 50 ml of acetonitrile is stirred for 3 hours and subsequently concentrated under waterpump vacuum. The residue is taken up in chloroform and the crystalline product is isolated by filtration with suction (product fraction 1). The mother liquor is washed with 1N hydrochloric acid and then with water, dried with sodium sulphate and filtered. The filtrate is concentrated under waterpump vacuum, the residue is digested with ethyl acetate and diethyl ether and the resulting crystalline product is isolated by filtration with suction (product fraction 2). The two product fractions are combined and stirred with 1N hydrochloric acid and ethyl acetate. The aqueous phase is extracted twice with ethyl acetate and the combined organic phases are dried with sodium sulphate and filtered. The filtrate is concentrated under waterpump vacuum, the residue is digested with diethyl ether and the resulting crystalline product is isolated by filtration with suction.

This gives 1.3 g (42% of theory) of 1-[4-cyano-5-(N-ethylsulphonyl-N-(3-(3,4-dichloro-phenyl)-propanoyl-amino)-2-fluoro-phenyl]-3-methyl-4-trifluoromethyl-3,6-dihydro-2,6-dioxo-1(2H)-pyrimidine of melting point 205° C.

Analogously to Preparation Example 1, and in accordance with the general description of the preparation process according to the invention, it is also possible to are, for example, the compounds of the formula (I) listed in Table 1 below.

TABLE 1

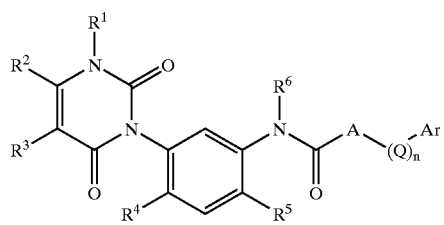

Examples of the compounds of the formula (I)

| Ex. No. | n | A | Ar | Q | $R^1$ | $R^2$ | $R^3$ | $R^4$ | $R^5$ | $R^6$ | Physical data |
|---|---|---|---|---|---|---|---|---|---|---|---|
| 2 | 1 | $CH_2$ | 3,4-dichlorophenyl | O | $CH_3$ | $CF_3$ | H | F | CN | $H_5C_2$-$SO_2$- | $^1$H-NMR: δ = 6.70 ppm ($D_6$-DMSO) |
| 3 | 1 | $CH_2$ | 3-methylphenyl | | $CH_3$ | $CF_3$ | H | F | CN | $H_5C_2$-$SO_2$- | m.p.: 219° C. |

TABLE 1-continued

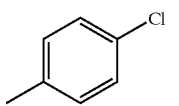

Examples of the compounds of the formula (I)

| Ex. No. | n | A | Ar | Q | R¹ | R² | R³ | R⁴ | R⁵ | R⁶ | Physical data |
|---|---|---|---|---|---|---|---|---|---|---|---|
| 4 | 1 | $CH_2$ | 4-Cl-phenyl | O | $CH_3$ | $CF_3$ | H | F | CN | $H_5C_2$-$SO_2$- | m.p.: 220° C. |
| 5 | 0 | $CH_2$ | 4-$OCH_3$-phenyl | — | $CH_3$ | $CF_3$ | H | F | CN | $H_5C_2$-$SO_2$- | m.p.: 125° C. |
| 6 | 1 | $CH_2$ | 3,4-di-Cl-phenyl | O | $CH_3$ | $CF_3$ | H | F | CN | $H_5C_2$-$SO_2$- | ¹H-NMR: δ = 6.70 ppm ($D_6$-DMSO) |
| 7 | 1 | $CH_2$ | 4-Cl-2-$CH_3$-phenyl | O | $CH_3$ | $CF_3$ | H | F | CN | $H_5C_2$-$SO_2$- | ¹H-NMR: δ = 7.25 ppm ($D_6$-DMSO) |
| 8 | 1 | $CH_2$ | 2-$NO_2$-phenyl | O | $CH_3$ | $CF_3$ | H | F | CN | $H_5C_2$-$SO_2$- | |
| 9 | 0 | $(CH_2)_2$ | phenyl | — | $CH_3$ | $CF_3$ | H | F | CN | $H_5C_2$-$SO_2$- | m.p.: 210° C. |
| 10 | 0 | $CH_2$ | 4-Cl-2-F-phenyl | — | $CH_3$ | $CF_3$ | H | F | CN | $H_5C_2$-$SO_2$- | |
| 11 | 0 | $CH_2$ | 2-Br-phenyl | — | $CH_3$ | $CF_3$ | H | F | CN | $H_5C_2$-$SO_2$- | |
| 12 | 0 | $CH_2$ | 4-F-2-Cl-phenyl | — | $CH_3$ | $CF_3$ | H | F | CN | $H_5C_2$-$SO_2$- | |

TABLE 1-continued

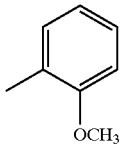

Examples of the compounds of the formula (I)

| Ex. No. | n | A | Ar | Q | R¹ | R² | R³ | R⁴ | R⁵ | R⁶ | Physical data |
|---|---|---|---|---|---|---|---|---|---|---|---|
| 13 | 0 | CH₂ | 2-methoxyphenyl (OCH₃) | — | CH₃ | CF₃ | H | F | CN | H₅C₂-SO₂- | |
| 14 | 1 | C₂H₅ (isobutyl) | phenyl | O | CH₃ | CF₃ | H | F | CN | H₅C₂-SO₂- | m.p.: 144° C. |
| 15 | 0 | CH₂ | 2,6-dichlorophenyl | — | CH₃ | CF₃ | H | F | CN | H₅C₂-SO₂- | |
| 16 | 0 | CH₂ | 4-CF₃-phenyl | — | CH₃ | CF₃ | H | F | CN | H₅C₂-SO₂- | m.p.: 192° C. |
| 17 | 0 | CH₂ | 3,5-dichloro-CF₃-phenyl | — | CH₃ | CF₃ | H | F | CN | H₅C₂-SO₂- | m.p.: 196° C. |
| 18 | 0 | CH₂ | 2-CF₃-phenyl | — | CH₃ | CF₃ | H | F | CN | H₅C₂-SO₂- | m.p.: 227° C. |
| 19 | 1 | CH₂ | 2-chlorophenyl | O | CH₃ | CF₃ | H | F | CN | H₅C₂-SO₂- | m.p.: 132° C. |
| 20 | 0 | CH₂ | 2,5-difluorophenyl | — | CH₃ | CF₃ | H | F | CN | H₅C₂-SO₂- | m.p.: 195° C. |

TABLE 1-continued

Examples of the compounds of the formula (I)

| Ex. No. | n | A | Ar | Q | R¹ | R² | R³ | R⁴ | R⁵ | R⁶ | Physical data |
|---|---|---|---|---|---|---|---|---|---|---|---|
| 21 | 0 | C₂H₅ (isobutyl) | phenyl | — | CH₃ | CF₃ | H | F | CN | H₅C₂-SO₂- | m.p.: 183° C. |
| 22 | 0 | CH₂ | 4-Cl-3-methyl-nitrobenzene (with NO₂) | — | CH₃ | CF₃ | H | F | CN | H₅C₂-SO₂- | |
| 23 | 1 | CH₃ (isobutyl) | 2,4-dichloro-5-methylphenyl | O | CH₃ | CF₃ | H | F | CN | H₅C₂-SO₂- | |
| 24 | 1 | CH₃ (isobutyl) | 2,4-dimethylphenyl (with CH₃) | O | CH₃ | CF₃ | H | F | CN | H₅C₂-SO₂- | |
| 25 | 1 | CH₃ (isobutyl) | 3-chloro-4-methylphenyl with CH₃ | O | CH₃ | CF₃ | H | F | CN | H₅C₂-SO₂- | |
| 26 | 1 | CH₃ (isobutyl) | 4-Cl-2-methyl-3-methylphenyl | O | CH₃ | CF₃ | H | F | CN | H₅C₂-SO₂- | |
| 27 | 1 | CH₂ | 4-Cl-2,3-dimethylphenyl | O | CH₃ | CF₃ | H | F | CN | H₃C-SO₂- | m.p.: 101° C. |

TABLE 1-continued

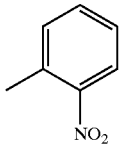

Examples of the compounds of the formula (I)

| Ex. No. | n | A | Ar | Q | R¹ | R² | R³ | R⁴ | R⁵ | R⁶ | Physical data |
|---|---|---|---|---|---|---|---|---|---|---|---|
| 28 | 1 | $CH_2$ | 2-NO₂-phenyl | O | $CH_3$ | $CF_3$ | H | F | CN | $H_7C_3\text{-}SO_2\text{-}$ | |
| 29 | 0 | $(CH_2)_2$ | 2-methylphenyl | — | $CH_3$ | $CF_3$ | H | F | CN | $H_7C_3\text{-}SO_2\text{-}$ | |
| 30 | 0 | $CH_2$ | 4-Cl-2-methylphenyl | — | $CH_3$ | $CF_3$ | H | F | CN | $H_7C_3\text{-}SO_2\text{-}$ | |
| 31 | 0 | $CH_2$ | 2-Br-phenyl | — | $CH_3$ | $CF_3$ | H | F | CN | $H_3C\text{-}SO_2\text{-}$ | m.p.: 131° C. |
| 32 | 0 | $CH_2$ | 4-F-phenyl | — | $CH_3$ | $CF_3$ | H | F | CN | $H_7C_3\text{-}SO_2\text{-}$ | |
| 33 | 0 | $CH_2$ | 2-OCH₃-phenyl | — | $CH_3$ | $CF_3$ | H | F | CN | $H_3C\text{-}SO_2\text{-}$ | |
| 34 | 1 | isobutyl ($C_2H_5$) | phenyl | O | $CH_3$ | $CF_3$ | H | F | CN | $H_3C\text{-}SO_2\text{-}$ | m.p.: 125° C. |
| 35 | 0 | $CH_2$ | 2,6-dichlorophenyl | — | $CH_3$ | $CF_3$ | H | F | CN | $H_3C\text{-}SO_2\text{-}$ | m.p.: 191° C. |
| 36 | 0 | $CH_2$ | 4-CF₃-phenyl | — | $CH_3$ | $CF_3$ | H | F | CN | $H_3C\text{-}SO_2\text{-}$ | |

TABLE 1-continued

Examples of the compounds of the formula (I)

| Ex. No. | n | A | Ar | Q | $R^1$ | $R^2$ | $R^3$ | $R^4$ | $R^5$ | $R^6$ | Physical data |
|---|---|---|---|---|---|---|---|---|---|---|---|
| 37 | 0 | $CH_2$ | 3,5-dichloro-4-methyl-(trifluoromethyl)phenyl (Cl, CF₃, Cl, CH₃ substituents) | — | $CH_3$ | $CF_3$ | H | F | CN | $H_3C-SO_2-$ | |
| 38 | 0 | $CH_2$ | 2-methyl-6-(trifluoromethyl)phenyl | — | $CH_3$ | $CF_3$ | H | F | CN | $H_3C-SO_2-$ | |
| 39 | 1 | $CH_2$ | 2-chloro-6-methylphenyl | O | $CH_3$ | $CF_3$ | H | F | CN | $H_3C-SO_2-$ | m.p.: 172° C. |
| 40 | 0 | $CH_2$ | 2,4-difluoro-5-methylphenyl | — | $CH_3$ | $CF_3$ | H | F | CN | $H_7C_3-SO_2-$ | |
| 41 | 0 | $C_2H_5$, isobutyl | phenyl | — | $CH_3$ | $CF_3$ | H | F | CN | $H_3C-SO_2-$ | m.p.: 81° C. |
| 42 | 0 | $CH_2$ | 4-chloro-3-methyl-nitrophenyl | — | $CH_3$ | $CF_3$ | H | F | CN | $H_3C-SO_2-$ | |
| 43 | 1 | $CH_3$, isobutyl | 2,4-dichloro-5-methylphenyl | O | $CH_3$ | $CF_3$ | H | F | CN | $H_3C-SO_2-$ | |

TABLE 1-continued
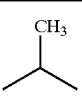
Examples of the compounds of the formula (I)
| Ex. No. | n | A | Ar | Q | $R^1$ | $R^2$ | $R^3$ | $R^4$ | $R^5$ | $R^6$ | Physical data |
|---|---|---|---|---|---|---|---|---|---|---|---|
| 44 | 1 | 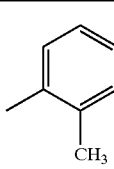 |  | O | $CH_3$ | $CF_3$ | H | F | CN |  | |
| 45 | 1 | 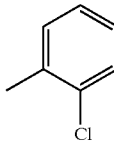 |  | O | $CH_3$ | $CF_3$ | H | F | CN |  | |
| 46 | 1 | 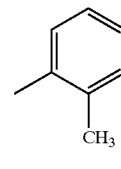 |  | O | $CH_3$ | $CF_3$ | H | F | CN | 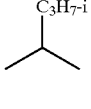 | |
| 47 | 0 | $C_3H_7$-i 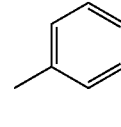 |  | — | $CH_3$ | $CF_3$ | H | F | CN | 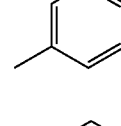 | m.p.: 118° C. |
| 48 | 0 | $CH_2$ |  | — | $CH_3$ | $CF_3$ | H | F | CN | 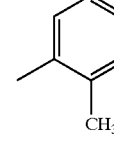 | m.p.: 168° C. |
| 49 | 0 | $CH_2$ |  | — | $CH_3$ | $CF_3$ | H | F | CN | 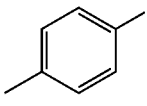 | m.p.: 182° C. |
| 50 | 0 | $CH_2$ |  | — | $CH_3$ | $CF_3$ | H | F | CN | 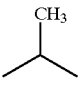 | m.p.: 131° C. |
| 51 | 0 | 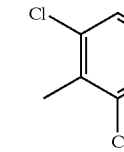 |  | — | $CH_3$ | $CF_3$ | H | F | CN | $H_5C_2$-$SO_2$- | m.p.: 237° C. |

TABLE 1-continued

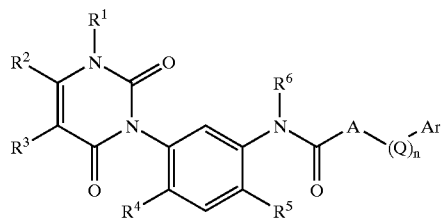

Examples of the compounds of the formula (I)

| Ex. No. | n | A | Ar | Q | R¹ | R² | R³ | R⁴ | R⁵ | R⁶ | Physical data |
|---|---|---|---|---|---|---|---|---|---|---|---|
| 52 | 1 | $C(CH_3)_2$ | 4-Cl-phenyl | O | $CH_3$ | $CF_3$ | H | F | CN | $H_5C_2$-$SO_2$- | m.p.: 105° C. |
| 53 | 1 | $CH(CH_3)$— (isobutyl-like) | phenyl | O | $CH_3$ | $CF_3$ | H | F | CN | $H_5C_2$-$SO_2$- | m.p.: 208° C. |
| 54 | 0 | $CH_2$ | phenyl | — | $CH_3$ | $CF_3$ | H | F | CN | $H_5C_2$-$SO_2$- | m.p.: 162° C. |
| 55 | 0 | $CH_2$ | 4-Cl-phenyl | — | $CH_3$ | $CF_3$ | H | F | CN | $H_5C_2$-$SO_2$- | m.p.: 211° C. |
| 56 | 0 | $CH_2$ | 2-Br-phenyl | — | $CH_3$ | $CF_3$ | H | F | CN | $H_5C_2$-$SO_2$- | m.p.: 204° C. |
| 57 | 0 | $CH_2$ | 4-F-phenyl | — | $CH_3$ | $CF_3$ | H | F | CN | $H_5C_2$-$SO_2$- | m.p.: 202° C. |
| 58 | 0 | $CH_2$ | 3,4-diF-phenyl | — | $CH_3$ | $CF_3$ | H | F | CN | $H_3C$-$SO_2$- | m.p.: 93° C. |
| 59 | 0 | $C(CH_3)_2$ | 4-Cl-phenyl | — | $CH_3$ | $CF_3$ | H | F | CN | $H_3C$-$SO_2$- | m.p.: 178° C. |
| 60 | 0 | $CH_2$ | phenyl | — | $CH_3$ | $CF_3$ | H | F | CN | $H_5C_2$-$SO_2$- | m.p.: 175° C. |
| 61 | 0 | $CH_2CH_2$ | phenyl | — | $CH_3$ | $CF_3$ | H | F | CN | $H_3C$-$SO_2$- | m.p.: 95° C. |

TABLE 1-continued
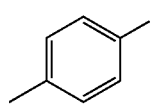
Examples of the compounds of the formula (I)
| Ex. No. | n | A | Ar | Q | R¹ | R² | R³ | R⁴ | R⁵ | R⁶ | Physical data |
|---|---|---|---|---|---|---|---|---|---|---|---|
| 62 | 0 | CH₂ |  | — | CH₃ | CF₃ | H | F | CN | H₃C–SO₂– | m.p.: 114° C. |
| 63 | 1 | CH₂ | 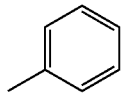 | O | CH₃ | CF₃ | H | F | CN | H₃C–SO₂– | m.p.: 125° C. |
| 64 | 1 | CH₂ |  | O | CH₃ | CF₃ | H | F | CN | H₃C–SO₂– | m.p.: 122° C. |
| 65 | 0 | CH₂CH₂ | 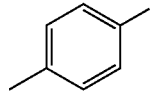 | — | CH₃ | CF₃ | H | F | CN | H₃C–SO₂– | m.p.: 97° C. |
| 66 | 0 | CH₂ |  | — | CH₃ | CF₃ | H | F | CN | H₃C–SO₂– | m.p.: 141° C. |
| 67 | 0 | CH₂ | 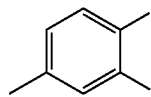 | — | CH₃ | CF₃ | H | F | CN | H₃C–SO₂– | m.p.: 127° C. |
| 68 | 0 | CH₂ |  | — | CH₃ | CF₃ | H | F | CN | H₃C–SO₂– | m.p.: 123° C. |
| 69 | 0 | CH₂ | 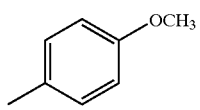 |  | CH₃ | CF₃ | H | F | CN | H₃C–SO₂– | m.p.: 165° C. |
| 70 | 1 |  | 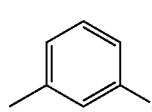 | O | CH₃ | CF₃ | H | F | CN | H₃C–SO₂– | m.p.: 201° C. |

Analogously, it is also possible to prepare the two compounds shown below:

Ex. No. 71

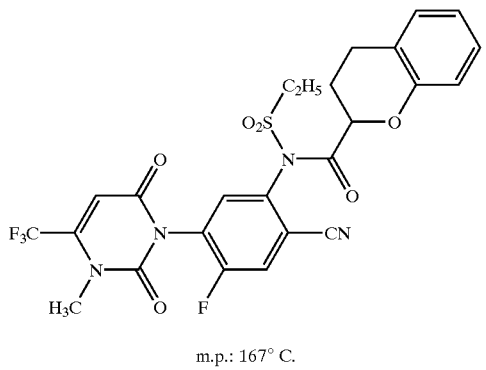

m.p.: 167° C.

Ex. No. 72

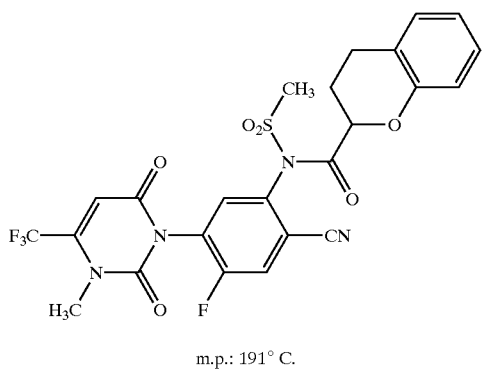

m.p.: 191° C.

USE EXAMPLES

Example A

Pre-emergence Test:

Solvent: 5 parts by weight of acetone

Emulsifier: 1 part by weight of alkylaryl polyglycol ether

To prepare a suitable preparation of active compound, 1 part by weight of active compound is mixed with the stated amount of solvent, the stated amount of emulsifier is added, and the concentrate is diluted with water to the desired concentration.

Seeds of the test plants are sown in normal soil. After approx. 24 hours, the soil is sprayed with the preparation of active compound in such a way that the desired amount of active compound is applied per unit area. The concentration of the spray mixture is chosen in such a way that the desired amount of active substance is applied in 1000 liters of water per hectare.

After spraying for three weeks, the degree of damage to the plants is scored in % damage in comparison with the development of the untreated control.

The figures denote:

0% = no action (like untreated control)
100% = total destruction

In this test, a very potent action against weeds is shown, for example, by the compound of Preparation Example 2.

Example B

Post-emergence Test

Solvent: 5 parts by weight of acetone

Emulsifier: 1 part by weight of alkylaryl polyglycol ether

To prepare a suitable preparation of active compound, 1 part by weight of active compound is mixed with the stated amount of solvent, the stated amount of emulsifier is added, and the concentrate is diluted with water to the desired concentration.

Test plants which have a height of 5 to 15 cm are sprayed with the preparation of active compound in such a way that the desired amounts of active compound are applied per unit area. The concentration of the spray mixture is chosen in such a way that the desired amounts of active substance are applied in 1000 liters of water per hectare.

After spraying for three weeks, the degree of damage to the plants is scored in % damage in comparison with the development of the untreated control.

The figures denote:

0% = no action (like untreated control)
100% = total destruction

In this test, a very potent action against weeds is shown, for example, by the compound of Preparation Example 2.

What is claimed is:

1. An acylaminophenyl-uracil of the formula (I)

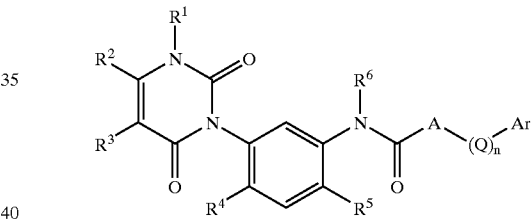

wherein n represents the numbers 0 or 1,

A represents unsubstituted or halogen-substituted alkanediyl(alkylene) having 1 to 6 carbon atoms or cycloalkanediyl having 3 to 6 carbon atoms, or A represents a single bond or an unsubstituted or halogen-substituted alkanediyl(alkylene) having 1 to 6 carbon atoms or cycloalkanediyl having 3 to 6 carbon atoms attached to Ar via an alkanediyl grouping having 1 to 3 carbon atoms where n represents 1;

Ar represents substituted aryl or arylalkyl having 6 or 10 carbon atoms in the aryl group and optionally 1 to 4 carbon atoms in the alkyl moiety, or represents unsubstituted or substituted heterocyclyl or heterocyclylalkyl selected from the group consisting of oxiranyl, oxiranylmethyl, oxetanyl, oxetanylmethyl, furyl, furylmethyl, tetrahydrofuryl, tetrahydrofurylmethyl, thienyl, thienylmethyl, tetrahydrothienyl, tetrahydrothienylmethyl, benzofuryl, benzofurylmethyl, dihydrobenzofuryl, dihydrobenzofurylmethyl, benzothienyl, benzothienylmethyl, pyrrolyl, pyrrolylmethyl, pyrazolyl, pyrazolylmethyl, pyranyl, pyranylmethyl, benzopyranyl, benzopyranylmethyl, dihydrobenzopyranyl, dihydrobenzopyranylmethyl, tetrahydrobenzopyranyl,
tetrahydrobenzopyranylmethyl, pyridinyl,
pyridinylmethyl, pyrimidinyl, and pyrimidinylmethyl,
wherein the substituent(s) for Ar is/are selected from
the group consisting of nitro, cyano, carboxyl,
carbamoyl, thiocarbamoyl, halogen, $C_1$–$C_4$-alkyl,
$C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, $C_1$–$C_4$-alkylamino, di-($C_1$–$C_4$-alkyl)amino, $C_1$–$C_4$-alkyl-carbonyl, $C_1$–$C_4$-alkoxy-carbonyl, $C_1$–$C_4$-alkylaminocarbonyl, di-($C_1$–$C_4$-alkyl)-amino-carbonyl, and di-($C_1$–$C_4$-alkyl)-amino-sulphonyl, Q represents O (oxygen), S (sulphur), SO, $SO_2$, NH or N($C_1$–$C_4$-alkyl), $R^1$ represents hydrogen, amino or unsubstituted or cyano-, carboxyl-, halogen-, $C_1$–$C_4$-alkoxy- or —$C_1$–$C_4$-alkoxycarbonyl-substituted alkyl having 1 to 6 carbon atoms, $R^2$ represents carboxyl, cyano, carbamoyl, thiocarbamoyl or represents unsubstituted or cyano-, halogen- or $C_1$–$C_4$-alkoxy-substituted alkyl or alkoxycarbonyl having 1 to 6 carbon atoms in the alkyl groups, $R^3$ represents hydrogen, halogen or unsubstituted or halogen-substituted alkyl having 1 to 6 carbon atoms, $R^4$ represents hydrogen, cyano, carbamoyl, thiocarbamoyl, or halogen, $R^5$ represents cyano, carbamoyl, thiocarbamoyl, halogen, or represents unsubstituted or halogen-substituted alkyl or alkoxy having 1 to 4 carbon atoms, and $R^6$ represents hydrogen, represents unsubstituted or cyano-, halogen- or $C_1$–$C_4$-alkoxy-substituted alkyl, alkylcarbonyl or alkoxycarbonyl having 1 to 6 carbon atoms in the alkyl groups, represents unsubstituted or halogen-substituted alkylsulphonyl having 1 to 6 carbon atoms, represents unsubstituted or halogen-substituted alkenyl, alkenylcarbonyl, alkenylsulphonyl or alkynyl having up to 6 carbon atoms, represents unsubstituted or halogen-substituted cycloalkylcarbonyl or cycloalkylsulphonyl having 3 to 6 carbon atoms in the cycloalkyl groups, represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$- halogenoalkylsulphonyl-, $C_1$–$C_4$-alkyl-carbonyl-, $C_1$–$C_4$-alkoxy-carbonyl- or di-($C_1$–$C_4$-alkyl-amino)-sulphonyl-substituted arylcarbonyl, arylsulphonyl, arylalkylcarbonyl or arylalkylsulphonyl having 6 or 10 carbon atoms in the aryl groups and 1 to 4 carbon atoms in the alkyl moiety, or represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxy-carbonyl- or di-($C_1$–$C_4$-alkyl-aminoysulphonyl-substituted heterocyclylcarbonyl or heterocyclylsulphonyl selected from the group consisting of furylcarbonyl, furylsulphonyl, thienylcarbonyl, thienylsulphonyl, pyrazolylcarbonyl, pyrazolylsulphonyl, pyridinylcarbonyl, pyridinylsulphonyl, quinolinylcarbonyl, quinolinylsulphonyl, pyrimidinylcarbonyl, and pyrimidinylsulphonyl.

2. The acylaminophenyl-uracil of claim 1, wherein
Ar represents substituted aryl or arylalkyl having 6 or 10 carbon atoms in the aryl group and optionally 1 to 4 carbon atoms in the alkyl moiety, wherein the Ar substituent(s) is/are selected from the group consisting of nitro, cyano, carboxyl, carbamoyl, thiocarbamoyl, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, $C_1$–$C_4$-alkylamino, di-($C_1$–$C_4$-alkyl)-amino, $C_1$–$C_4$-alkyl-carbonyl, $C_1$–$C_4$-alkoxy-carbonyl, $C_1$–$C_4$-alkylamino-carbonyl, di-($C_1$–$C_4$-alkyl)-amino-carbonyl, and di-($C_1$–$C_4$-alkyl)-amino-sulphonyl.

3. An acylaminophenyl-uracil of the formula (I),

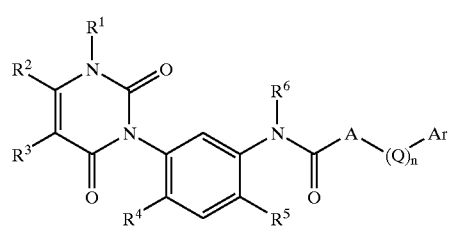

wherein
n represents the numbers 0 or 1,
A represents unsubstituted or fluorine- and/or chlorine-substituted methylene, ethane-1,1-diyl(ethylidene), ethane-1,2-diyl(dimethylene), propane-1,1-diyl (propylidene), propane-1,2-diyl or propane-1,3-diyl (trimethylene), cyclopropane-1,1-diyl, cyclopropane-1, 2-diyl, cyclobutane-1,1-diyl, cyclopentane-1,1-diyl or cyclohexane-1,1-diyl, or
A represents a single bond, or an unsubstituted or fluorine- and/or chlorine-substituted methylene, ethane-1,1-diyl (ethylidene), ethane-1,2-diyl(dimethylene), propane-1, 1-diyl(propylidene), propane-1,2-diyl or propane-1,3-diyl(trimethylene), cyclopropane-1,1-diyl, cyclopropane-1,2-diyl, cyclobutane-1,1-diyl, cyclopentane-1,1-diyl or cyclohexane-1,1-diyl, attached to Ar via a 1,2-ethanediyl(dimethylene) grouping where n represents 1;
Ar represents substituted phenyl, naphthyl, benzyl, 1-phenyl-ethyl, 2-phenyl-ethyl, 1-phenyl-propyl, 2-phenyl-propyl or 3-phenyl-propyl, or represents an optionally substituted heterocyclyl or heterocyclylalkyl selected from the group consisting of oxiranyl, oxiranylmethyl, oxetanyl, oxetanylmethyl, furyl, furylmethyl, tetrahydrofuryl, tetrahydrofurylmethyl, thienyl, thienylmethyl, tetrahydrothienyl, tetrahydrothienylmethyl, benzofuryl, benzofurylmethyl, dihydrobenzofuryl, dihydrobenzofurylmethyl, benzothienyl, benzothienylmethyl, pyrrolyl, pyrrolylmethyl, pyrazolyl, pyrazolylmethyl, pyranyl, pyranylmethyl, benzopyranyl, benzopyranylmethyl, dihydrobenzopyranyl, dihydrobenzopyranylmethyl, tetrahydrobenzopyranyl, tetrahydrobenzopyranylmethyl, pyridinyl, pyridinylmethyl, pyrimidinyl, and pyrimidinylmethyl, wherein the Ar substituent(s) is/are selected from the group consisting of nitro, cyano, carboxyl, carbamoyl, thiocarbamoyl, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, methylthio, ethylthio, n- or i-propylthio, n-, i-, s- or t-butylthio, difluoromethylthio, trifluoromethylthio, methylsulphinyl, ethylsulphfinyl, n- or i-propylsulphinyl, trifluoromethylsulphinyl, methylsulphonyl, ethylsulphonyl, n- or i-propylsulphonyl, trifluoromethylsulphonyl, methylamino, ethylamino, n- or i-propylamino, n-, i-, s- or t-butylamino, dimethylamino, diethyl-amino, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, dimethylaminocarbonyl, diethylaminocarbonyl, dimethylaminosulphonyl, and diethylaminosulphonyl, Q represents O (oxygen), S (sulphur), SO, $SO_2$, NH or N(methyl), $R^1$ represents hydrogen, amino or unsubstituted or cyano-, fluorine-, chlorine-, methoxy- or ethoxy-substituted methyl or ethyl, $R^2$ represents carboxyl, cyano, carbamoyl, thiocarbamoyl or represents unsubstituted or cyano-, fluorine-, chlorine-, methoxy- or ethoxy-substituted methyl, ethyl, n- or i-propyl, methoxycarbonyl or ethoxycarbonyl, $R^3$ represents hydrogen, fluorine, chlorine, bromine or unsubstituted or fluorine- or chlorine-substituted methyl, ethyl, n- or i-propyl, $R^4$ represents hydrogen, cyano, carbamoyl, thiocarbamoyl, fluorine or chlorine, $R^5$ represents cyano, carbamoyl, thiocarbamoyl, fluorine, chlorine, bromine, or represents unsubstituted or fluorine- and/or chlorine-substituted methyl, ethyl, n- or i-propyl, methoxy, ethoxy, n- or i-propoxy, and $R^6$ represents hydrogen, represents unsubstituted or cyano-, fluorine-, chlorine-, methoxy- or ethoxy-substituted methyl, ethyl, n- or i-propyl, n-, i-, s- or t-butyl, acetyl, propionyl, n- or i-butyroyl, n-, i- or sec-valeroyl, pivaloyl, methoxycarbonyl, ethoxycarbonyl, n- or i-propoxycarbonyl, represents optionally fluorine- and/or chlorine-substituted methylsulphonyl, ethylsulphonyl, n- or i-propylsulphonyl, n-, i-, s- or t-butylsulphonyl, represents optionally fluorine-, chlorine- and/or bromine-substituted ethenyl, propenyl, butenyl, ethenylcarbonyl, propenylcarbonyl, butenylcarbonyl, ethynyl, propynyl or butynyl, represents optionally fluorine-, chlorine- and/or bromine-substituted cyclopropylcarbonyl, cyclopropylmethylcarbonyl, cyclobutylcarbonyl, cyclobutylmethylcarbonyl, cyclopentylcarbonyl, cyclopentylmethylcarbonyl, cyclohexylcarbonyl, cyclohexylmethylcarbonyl, cyclopropylsulphonyl, cyclopropylmethylsulphonyl, cyclobutylsulphonyl, cyclobutylmethylsulphonyl, cyclopentylsulphonyl, cyclopentylmethylsulphonyl, cyclohexylsulphonyl or cyclohexylmethylsulphonyl, represents optionally nitro-, cyano-, fluorine-, chlorine-, bromine-, methyl-, ethyl-, n- or i-propyl-, n-, i-, s- or t-butyl, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, acetyl-, propionyl-, n- or i-butyroyl-, methoxycarbonyl-, ethoxycarbonyl-, n- or i-propoxycarbonyl-, dimethylaminosulphonyl- or diethylaminosulphonyl-substituted benzoyl, phenylsulphonyl, phenylacetyl, phenylpropionyl, benzylsulphonyl or phenylethylsulphonyl, or represents optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, acetyl-, propionyl-, n- or i-butyroyl-, methoxycarbonyl-, ethoxycarbonyl-, n- or i-propoxy-carbonyl-, dimethylaminosulphonyl- or diethylaminosulphonyl-substituted heterocyclylcarbonyl or heterocyclylsulphonyl selected from the group consisting of furylcarbonyl, furylsulphonyl, thienylcarbonyl, thienylsulphonyl, pyrazolylcarbonyl, pyrazolylsulphonyl, pyridinylcarbonyl, pyridinylsulphonyl, quinolinylcarbonyl, quinolinylsulphonyl, pyrimidinylcarbonyl, and pyrimidinylsulphonyl.

4. The acylaminophenyl-uracil of claim 1, wherein n represents the number 1,

A represents methylene, ethane-1,1-diyl(ethylidene) or ethane-1,2-diyl(dimethylene), Ar represents substituted phenyl, naphthyl or benzyl, wherein the Ar substituent(s) is/are selected from the group consisting of nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy, trifluoromethoxy, methylthio, ethylthio, n- or i-propylthio, difluoromethylthio, trifluoromethylthio, methylsulphinyl, ethylsulphinyl, n- or i-propylsulphinyl, trifluoromethylsulphinyl, methylsulphonyl, ethyl-sulphonyl, n- or i-propylsulphonyl, trifluoromethylsulphonyl, methoxycarbonyl, ethoxycarbonyl, and n- or i-propoxycarbonyl, Q represents O (oxygen), $R^1$ represents hydrogen, amino or methyl, $R^2$ represents trifluoromethyl, $R^3$ represents hydrogen, chlorine or methyl, $R^4$ represents hydrogen, fluorine or chlorine, $R^5$ represents cyano, carbamoyl, thiocarbamoyl, chlorine or bromine, $R^6$ represents hydrogen, represents unsubstituted or fluorine- and/or chlorine-substituted methylsulphonyl, ethylsulphonyl, n- or i-propylsulphonyl, n-, i- s- or t-butylsulphonyl, or represents optionally fluorine- and/or chlorine-substituted cyclopropylsulphonyl.

5. The acylaminophenyl-uracil of claim 1, wherein n represents the number 0,

A represents methylene, ethane-1,1-diyl(ethylidene) or ethane-1,2-diyl(dimethylene), Ar represents substituted phenyl or naphthyl,
wherein the Ar substituent(s) is/are selected from the group consisting of nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy, trifluoromethoxy, methylthio, ethylthio, n- or i-propylthio, difluoromethylthio, trifluoromethylthio, methylsulphinyl, ethylsulphinyl, n- or i-propylsulphinyl, trifluoromethylsulphinyl, methylsulphonyl, ethylsulphonyl, n- or i-propylsulphonyl, trifluoromethylsulphonyl, methoxycarbonyl, ethoxycarbonyl, and n- or i-propoxycarbonyl, $R^1$ represents hydrogen, amino or methyl, $R^2$ represents trifluoromethyl, $R^3$ represents hydrogen, chlorine or methyl, $R^4$ represents hydrogen, fluorine or chlorine, $R^5$ represents cyano, carbamoyl, thiocarbamoyl, chlorine or bromine, and $R^6$ represents hydrogen, represents unsubstituted or fluorine- and/or chlorine-substituted methylsulphonyl, ethylsulphonyl, n- or i-propylsulphonyl, n-, i-, s- or t-butylsulphonyl, or represents optionally fluorine- and/ or chlorine-substituted cyclopropylsulphonyl.

6. A process for preparing an acylaminophenyl-uracil of formula I

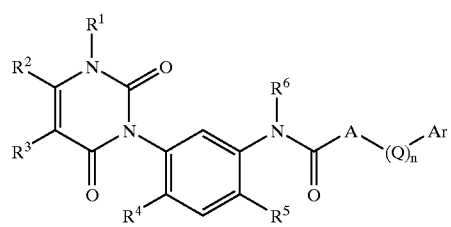

(I)

wherein n represents the number 1,

A represents unsubstituted or halogen-substituted alkanediyl(alkylene) having 1 to 6 carbon atoms or cycloalkanediyl having 3 to 6 carbon atoms, or A represents a single bond or an unsubstituted or halogen-substituted alkanediyl(alkylene) having 1 to 6 carbon atoms or cycloalkanediyl having 3 to 6 carbon atoms attached to Ar via an alkanediyl grouping having 1 to 3 carbon atoms where n represents 1;

Ar represents substituted aryl or arylalkyl having 6 or 10 carbon atoms in the aryl group and optionally 1 to 4 carbon atoms in the alkyl moiety, or represents unsubstituted or substituted heterocyclyl or heterocyclylalkyl selected from the group consisting of oxiranyl, oxiranylmethyl, oxetanyl, oxetanylmethyl, furyl, furylmethyl, tetrahydrofuryl, tetrahydrofurylmethyl, thienyl, thienylmethyl, tetrahydrothienyl, tetrahydrothienylmethyl, benzofuryl, benzofurylmethyl, dihydrobenzofuryl, dihydrobenzofurylmethyl, benzothienyl, benzothienylmethyl, pyrrolyl, pyrrolylmethyl, pyrazolyl, pyrazolylmethyl, pyranyl, pyranylmethyl, benzopyranyl, benzopyraiiylmethyl, dihydrobenzopyranyl, dihydrobenzopyranylmethyl, tetrahydrobenzopyranyl, tetrahydrobenzopyranylmethyl, pyridinyl, pyridinylmethyl, pyrimidinyl, and pyrimidinylmethyl,
wherein the substituent(s) for Ar is/are selected from the group consisting of nitro, cyano, carboxyl, carbamoyl, thiocarbamoyl, halogen, $C_1$–$C_4$-alkyl, $C_1$–$C_4$-halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, $C_1$–$C_4$-alkylamino, di-($C_1$–$C_4$-alkyl)amino, $C_1$–$C_4$-alkyl-carbonyl, $C_1$–$C_4$-alkoxy-carbonyl, $C_1$–$C_4$-alkylamino-carbonyl, di-($C_1$–$C_4$-alkylamino-carbonyl, and di-($C_1$–$C_4$-alkyl)-amino-sulphonyl, Q represents O (oxygen), S (sulphur), SO, $SO_2$, NH or N($C_1$–$C_4$-alkyl), $R^1$ represents hydrogen, amino or unsubstituted or cyano-, carboxyl-, halogen-, $C_1$–$C_4$-alkoxy- or —$C_1$–$C_4$-alkoxycarbonyl-substituted alkyl having 1 to 6 carbon atoms, $R^2$ represents carboxyl, cyano, carbamoyl, thiocarbamoyl or represents unsubstituted or cyano-, halogen- or $C_1$–$C_4$-alkoxy-substituted alkyl or alkoxycarbonyl having 1 to 6 carbon atoms in the alkyl groups, $R^3$ represents hydrogen, halogen or unsubstituted or halogen-substituted alkyl having 1 to 6 carbon atoms, $R^4$ represents hydrogen, cyano, carbamoyl, thiocarbamoyl, or halogen, $R^5$ represents cyano, carbamoyl, thiocarbamoyl, halogen, or represents unsubstituted or halogen-substituted alkyl or alkoxy having 1 to 4 carbon atoms, and $R^6$ represents hydrogen, represents unsubstituted or cyano-, halogen- or $C_1$–$C_4$-alkoxy-substituted alkyl, alkylcarbonyl or alkoxycarbonyl having 1 to 6 carbon atoms in the alkyl groups, represents unsubstituted or halogen-substituted alkylsulphonyl having 1 to 6 carbon atoms, represents unsubstituted or halogen-substituted alkenyl, alkenylcarbonyl, alkenylsulphonyl or alkynyl having up to 6 carbon atoms, represents unsubstituted or halogen-substituted cycloalkylcarbonyl or cycloalkylsulphonyl having 3 to 6 carbon atoms in the cycloalkyl groups, represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl, $C_1$–$C_4$-alkylcarbonyl-, $C_1$–$C_4$-alkoxy-carbonyl- or di-($C_1$–$C_4$-alkyl-aminoysulphonyl-substituted arylcarbonyl, arylsulphonyl, arylalkylcarbonyl or arylalkylsulphonyl having 6 or 10 carbon atoms in the aryl groups and 1 to 4 carbon atoms in the alkyl moiety, or represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkylcarbonyl-, $C_1$–$C_4$-alkoxy-carbonyl- or di-($C_1$–$C_4$-alkyl-amino)-sulphonyl-substituted heterocyclylcarbonyl or heterocyclylsulphonyl selected from the group consisting of furylcarbonyl, furylsulphonyl, thienylcarbonyl, thienylsulphonyl, pyrazolylcarbonyl, pyrazolylsulphonyl, pyridinylcarbonyl, pyridinylsulphonyl, quinolinylcarbonyl, quinolinylsulphonyl, pyrimidinylcarbonyl, and pyrimidinylsulphonyl, or, wherein n represents the number 0, $R^1$, $R^2$, $R^3$, $R^4$, $R^5$ n, A, Ar and Q are as defined above, and $R^6$ represents unsubstituted or halogen-substituted alkenylsulphonyl having up to 6 carbon atoms, represents unsubstituted or halogen-substituted cycloalkylsulphonyl having 3 to 6 carbon atoms in the cycloalkyl groups, represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxycarbonyl- or di-($C_1$–$C_4$-alkyl-amino)-sulphonyl-substituted arylsulphonyl, or arylalkylsulphonyl having 6 or 10 carbon atoms in the aryl groups and 1 to 4 carbon atoms in the alkyl moiety, or represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxy-carbonyl- or di-($C_1$–$C_4$-alkyl-amino)-sulphonyl-substituted heterocyclylsulphonyl selected from the group consisting of furylcarbonyl, furylsulphonyl, thienylcarbonyl, thienylsulphonyl, pyrazolylcarbonyl, pyrazolylsulphonyl, pyridinylcarbonyl, pyridinylsulphonyl, quinolinylcarbonyl, quinolinylsulphonyl, pyrimidinylcarbonyl, and pyrimidinylsulphonyl;

said process comprising reacting an aminophenyl-uracil of the formula (I)

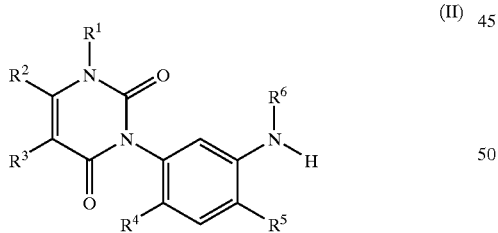

(II)

wherein $R^1$, $R^2$, $R^3$, $R^4$, $R^5$ and $R^6$ are as defined above with a compound of the formula (III)

(III)

wherein n, A, Ar and Q are as defined above, and

X represents halogen, and collecting the reaction product.

7. A method for controlling the growth of at least one plant comprising applying to said plant and/or its locus an effective amount of one or more acylaminophenyl-uracil(s) of claim 1.

8. A herbicidal composition, comprising one or more acylaminophenyluracil(s) of claim 1 and one or more extenders.

9. The process of claim 6, wherein

Ar represents substituted aryl or arylalkyl having 6 or 10 carbon atoms in the aryl group and optionally 1 to 4 carbon atoms in the alkyl moiety, wherein the Ar substituent(s) is/are selected from the group consisting of: nitro, cyano, carboxyl, carbamoyl, thiocarbamoyl, halogen, $C_1$–$C_4$-alkyl, $C_1$–$C_4$ halogenoalkyl, $C_1$–$C_4$-alkoxy, $C_1$–$C_4$-halogenoalkoxy, $C_1$–$C_4$-alkylthio, $C_1$–$C_4$-halogenoalkylthio, $C_1$–$C_4$-alkylsulphinyl, $C_1$–$C_4$-halogenoalkylsulphinyl, $C_1$–$C_4$-alkylsulphonyl, $C_1$–$C_4$-halogenoalkylsulphonyl, $C_1$–$C_4$-alkylamino, di-($C_1$–$C_4$-alkyl)-amino, $C_1$–$C_4$-alkyl-carbonyl, $C_1$–$C_4$-alkoxy-carbonyl, $C_1$–$C_4$-alkylamino-carbonyl, di-($C_1$–$C_4$-alkyl)-amino-carbonyl, and di-($C_1$–$C_4$-alkyl)-amino-sulphonyl.

10. The process of claim 6, wherein

A represents unsubstituted or fluorine- and/or chlorine-substituted methylene, ethane-1,1-diyl(ethylidene), ethane-1,2-diyl(dimethylene), propane-1,1-diyl (propylidene), propane-1,2-diyl or propane-1,3-diyl (trimethylene), cyclopropane-1,1-diyl, cyclopropane-1,2-diyl, cyclobutane-1,1-diyl, cyclopentane-1,1-diyl or cyclohexane-1,1-diyl, with the proviso that where n represents 1 A represents a single bond, or an unsubstituted or fluorine- and/or chlorine-substituted methylene, ethane-1,1-diyl(ethylidene), ethane-1,2-diyl(dimethylene), propane-1,1-diyl(propylidene), propane-1,2-diyl or propane-1,3-diyl(trimethylene), cyclopropane-1,1-diyl, cyclopropane-1,2-diyl, cyclobutane-1,1-diyl, cyclopentane-1,1-diyl or cyclohexane-1,1-diyl, attached to Ar via a 1,2-ethanediyl(dimethylene) grouping;

Ar represents substituted phenyl, naphthyl, benzyl, 1-phenyl-ethyl, 2-phenyl-ethyl, 1-phenyl-propyl, 2-phenyl-propyl or 3-phenyl-propyl, or represents optionally substituted heterocyclyl or heterocyclylalkyl selected from the group consisting of oxiranyl, oxiranylmethyl, oxetanyl, oxetanylmethyl, furyl, furylmethyl, tetrahydrofuryl, tetrahydrofurylmethyl, thienyl, thienylmethyl, tetrahydrothienyl, tetrahydrothienylmethyl, benzofuryl, benzofurylmethyl, dihydrobenzofuryl, dihydrobenzofurylmethyl, benzothienyl, benzothienylmethyl, pyrrolyl, pyrrolylmethyl, pyrazolyl, pyrazolylmethyl, pyranyl, pyranylmethyl, benzopyranyl, benzopyranylmethyl, dihydrobenzopyranyl, dihydrobenzopyranylmethyl, tetrahydrobenzopyranyl, tetrahydrobenzopyranylmethyl, pyridinyl, pyridinylmethyl, pyrimidinyl, and pyrimidinylmethyl, wherein the Ar substituent(s) is/are selected from the group consisting of nitro, cyano, carboxyl, carbamoyl, thiocarbamoyl, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, methylthio, ethylthio, n- or i-propylthio, n-, i-, s- or t-butylthio, difluoromethylthio, trifluoromethylthio, methylsulphinyl, ethylsulphonyl, n- or i-propylsulphinyl, trifluoromethylsulphinyl, methylsulphonyl, ethylsulphonyl, n- or i-propylsulphonyl, trifluoromethylsulphonyl, methylamino, ethylamino, n- or i-propylamino, n-, i-, s- or t-butylamino, dimethylamino, diethyl-amino, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, dimethylaminocarbonyl, diethylaminocarbonyl, dimethylaminosulphonyl, and diethylaminosulphonyl.

11. The process of claim 6, wherein n represents the number 1,

A represents methylene, ethane-1,1-diyl(ethylidene) or ethane-1,2-diyl(dimethylene), Ar represents substituted phenyl, naphthyl or benzyl,
wherein the Ar substituent(s) is/are selected from the group consisting of nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy, trifluoromethoxy, methylthio, ethylthio, n- or i-propylthio, difluoromethylthio, trifluoromethylthio, methylsulphinyl, ethylsulphinyl, n- or i-propylsulphinyl, trifluoromethylsulphinyl, methylsulphonyl, ethylsulphonyl, n- or i-propylsulphonyl, trifluoromethylsulphonyl, methoxycarbonyl, ethoxycarbonyl, and n- or i-propoxycarbonyl, Q represents O (oxygen).

12. The process of claim 6, wherein n represents the number 0,

A represents methylene, ethane-1,1-diyl(ethylidene) or ethane-1,2-diyl(dimethylene), Ar represents substituted phenyl or naphthyl,
wherein the Ar substituent(s) is/are selected from the group consisting of nitro, cyano, fluorine, chlorine, bromine, methyl, ethyl, n- or i-propyl, n-, i-, s- or t-butyl, trifluoromethyl, methoxy, ethoxy, n- or i-propoxy, difluoromethoxy, trifluoromethoxy, methylthio, ethylthio, n- or i-propylthio, difluoromethylthio, trifluoromethylthio, methylsulphinyl, ethylsulphinyl, n- or i-propylsulphinyl, trifluoromethylsulphinyl, methylsulphonyl, ethylsulphonyl, n- or i-propylsulphonyl, trifluoromethylsulphonyl, methoxycarbonyl, ethoxycarbonyl, and n- or i-propoxycarbonyl.

13. The method of claim 7, wherein the acylaminophenyluracil is applied at a rate of between 1 and 10 kg per hectare of soil surface.

14. The acylaminophenyl-uracil of claim 1 wherein $R^6$ represents unsubstituted or halogen-substituted alkylsulphonyl having 1 to 6 carbon atoms, represents unsubstituted or halogen-substituted alkenylsulphonyl having 1 to 6 carbon atoms, represents unsubstituted or halogen-substituted cycloalkylsulphonyl having 3 to 6 carbon atoms in the cycloalkyl groups, represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxy-carbonyl- or di-($C_1$–$C_4$-alkyl-amino)-sulphonyl-substituted arylsulphonyl, or arylalkylsulphonyl having 6 or 10 carbon atoms in the aryl groups and 1 to 4 carbon atoms in the alkyl moiety, or represents unsubstituted or nitro-, cyano-, halogen-, $C_1$–$C_4$-alkyl-, $C_1$–$C_4$-halogenoalkyl-, $C_1$–$C_4$-alkoxy-, $C_1$–$C_4$-halogenoalkoxy-, $C_1$–$C_4$-alkylthio-, $C_1$–$C_4$-halogenoalkylthio-, $C_1$–$C_4$-alkylsulphinyl-, $C_1$–$C_4$-halogenoalkylsulphinyl-, $C_1$–$C_4$-alkylsulphonyl-, $C_1$–$C_4$-halogenoalkylsulphonyl-, $C_1$–$C_4$-alkyl-carbonyl-, $C_1$–$C_4$-alkoxy-carbonyl- or di-(($C_1$–$C_4$-alkyl-amino)-sulphonyl-substituted heterocyclylsulphonyl selected from the group consisting of furylsulphonyl, thienylsulphonyl, pyrazolylsulphonyl, pyridinylsulphonyl, quinolinylsulphonyl, and pyrimidinylsulphonyl.

15. An acylaminophenyl-uracil of the formula (I),

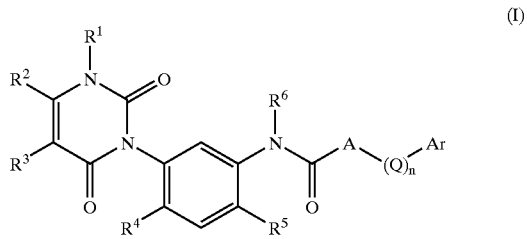

wherein n represents the numbers 0 or 1,

A represents unsubstituted or halogen-substituted alkanediyl(alkylene) having 1 to 6 carbon atoms or cycloalkanediyl having 3 to 6 carbon atoms, or A represents a single bond or an unsubstituted or halogen-substituted alkanediyl(alkylene) having 1 to 6 carbon atoms or cycloalkanediyl having 3 to 6 carbon atoms attached to Ar via an alkanediyl grouping having 1 to 3 carbon atoms where n represents 1;

Ar represents substituted phenyl, naphthyl, benzyl, 1-phenyl-ethyl, 2-phenyl-ethyl, 1-phenyl-propyl, 2-phenyl-propyl or 3-phenyl-propyl, or represents optionally substituted heterocyclyl or heterocyclylalkyl selected from the group consisting of oxiranyl, oxiranylmethyl, oxetanyl, oxetanylmethyl, furyl, furylmethyl, tetrahydrofuryl, tetrahydrofurylmethyl, thienyl, thienylmethyl, tetrahydrothienyl, tetrahydrothienylmethyl, benzofuryl, benzofurylmethyl, dihydrobenzofuryl, dihydrobenzofurylmethyl, benzothienyl, benzothienylmethyl, pyrrolyl, pyrrolylmethyl, pyrazolyl, pyrazolylmethyl, pyranyl, pyranylmethyl, benzopyranyl, benzopyranylmethyl, dihydrobenzopyranyl, dihydrobenzopyranylmethyl, tetrahydrobenzopyranyl, tetrahydrobenzopyranylmethyl, pyridinyl, pyridinylmethyl, pyrimidinyl, and pyrimidinylmethyl, wherein the Ar substituent(s) is/are selected from the group consisting of nitro, cyano, carboxyl, carbamoyl, thiocarbamoyl, fluorine, chlorine, bromine, methyl, ethyl, n- or i-propyl, n-, i-, s- or t-butyl, trifluoromethyl, methoxy, ethoxy, n- or i-propoxy, n-, i-, s- or t-butoxy, difluoromethoxy, trifluoromethoxy, methylthio, ethylthio, n- or i-propylthio, n-, i-, s- or t-butylthio, difluoromethylthio, trifluoromethylthio, methylsulphinyl, ethylsulphinyl, n- or i-propylsulphinyl, trifluoromethylsulphinyl, methylsulphonyl, ethylsulphonyl, n- or i-propylsulphonyl, trifluoromethylsulphonyl, methylamino, ethylamino, n- or i-propylamino, n-, i-, s- or t-butylamino, dimethylamino, diethyl-amino, acetyl, propionyl, n- or i-butyroyl, methoxycarbonyl, ethoxycarbonyl, n- or i-propoxycarbonyl, methylaminocarbonyl, ethylaminocarbonyl, n- or i-propylaminocarbonyl, dimethylaminocarbonyl, diethylaminocarbonyl, dimethylaminosulphonyl, and diethylaminosulphonyl, Q represents O (oxygen), S (sulphur), SO, $SO_2$, NH or $N(C_1-C_4$-alkyl), $R^1$ represents hydrogen, amino or unsubstituted or cyano-, carboxyl-, halogen-, $C_1-C_4$-alkoxy- or —$C_1-C_4$-alkoxycarbonyl-substituted alkyl having 1 to 6 carbon atoms, $R^2$ represents carboxyl, cyano, carbamoyl, thiocarbamoyl or represents unsubstituted or cyano-, halogen- or $C_1-C_4$-alkoxy-substituted alkyl or alkoxycarbonyl having 1 to 6 carbon atoms in the alkyl groups, $R^3$ represents hydrogen, halogen or unsubstituted or halogen-substituted alkyl having 1 to 6 carbon atoms, $R^4$ represents hydrogen, cyano, carbamoyl, thiocarbamoyl, or halogen, $R^5$ represents cyano, carbamoyl, thiocarbamoyl, halogen, or represents unsubstituted or halogen-substituted alkyl or alkoxy having 1 to 4 carbon atoms, and $R^6$ represents hydrogen, represents unsubstituted or cyano-, fluorine-, chlorine-, methoxy- or ethoxy-substituted methyl, ethyl, n- or i-propyl, n-, i-, s- or t-butyl, acetyl, propionyl, n- or i-butyroyl, n-, i- or sec-valeroyl, pivaloyl, methoxycarbonyl, ethoxycarbonyl, n- or i-propoxy-carbonyl, represents optionally fluorine- and/or chlorine-substituted methylsulphonyl, ethylsulphonyl, n- or i-propylsulphonyl, n-, i-, s- or t-butylsulphonyl, represents optionally fluorine-, chlorine- and/or bromine-substituted ethenyl, propenyl, butenyl, ethenylcarbonyl, propenylcarbonyl, butenylcarbonyl, ethynyl, propynyl or butynyl, represents optionally fluorine-, chlorine- and/or bromine-substituted cyclopropylcarbonyl, cyclopropylmethylcarbonyl, cyclobutylcarbonyl, cyclobutylmethylcarbonyl, cyclopentylcarbonyl, cyclopentylmethylcarbonyl, cyclohexylcarbonyl, cyclohexylmethylcarbonyl, cyclopropylsulphonyl, cyclopropylmethylsulphonyl, cyclobutylsulphonyl, cyclobutylmethylsulphonyl, cyclopentylsulphonyl, cyclopentylmethylsulphonyl, cyclohexylsulphonyl or cyclohexylmethylsulphonyl, represents optionally nitro-, cyano-, fluorine-, chlorine-, bromine-, methyl-, ethyl-, n- or i-propyl-, n-, i-, s- or t-butyl, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, acetyl-, propionyl-, n- or i-butyroyl-, methoxycarbonyl-, ethoxycarbonyl-, n- or i-propoxycarbonyl-, dimethylaminosulphonyl- or diethylamino-sulphonyl-substituted benzoyl, phenylsulphonyl, phenylacetyl, phenylpropionyl, benzylsulphonyl or phenylethylsulphonyl, or represents optionally nitro-, cyano-, fluorine-, chlorine-, bromine-, methyl-, ethyl-, n- or i-propyl-, n-, i-, s- or t-butyl-, trifluoromethyl-, methoxy-, ethoxy-, n- or i-propoxy-, n-, i-, s- or t-butoxy-, difluoromethoxy-, trifluoromethoxy-, methylthio-, ethylthio-, n- or i-propylthio-, n-, i-, s- or t-butylthio-, difluoromethylthio-, trifluoromethylthio-, methylsulphinyl-, ethylsulphinyl-, n- or i-propylsulphinyl-, trifluoromethylsulphinyl-, methylsulphonyl-, ethylsulphonyl-, n- or i-propylsulphonyl-, trifluoromethylsulphonyl-, acetyl-, propionyl-, n- or i-butyroyl-, methoxycarbonyl-, ethoxycarbonyl-, n- or i-propoxy-carbonyl-, dimethylaminosulphonyl- or diethyl-aminosulphonyl-substituted heterocyclylcarbonyl or heterocyclylsulphonyl selected from the group consisting of furylcarbonyl, furylsulphonyl, thienylcarbonyl, thienylsulphonyl, pyrazolylcarbonyl, pyrazolylsulphonyl, pyridinylcarbonyl, pyddinylsulphonyl, quinolinylcarbonyl, quinolinylsulphonyl, pyrimidinylcarbonyl, and pyrimidinylsulphonyl.

16. An acylaminophenyl-uracil of the formula

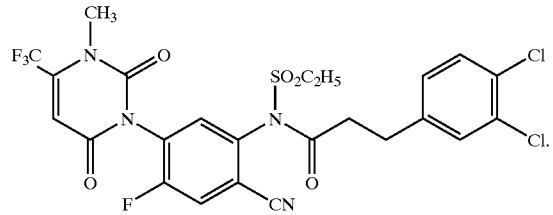

17. An acylaminophenyl-uracil of the formula

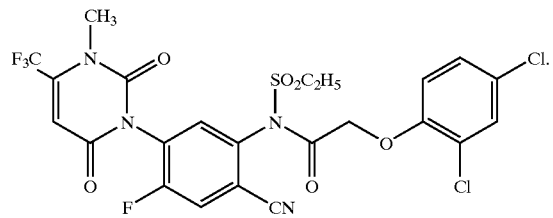

18. An acylaminophenyl-uracil of the formula

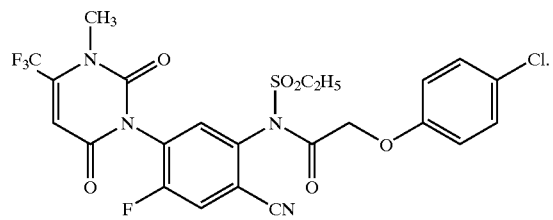

19. An acylaminophenyl-uracil of the formula

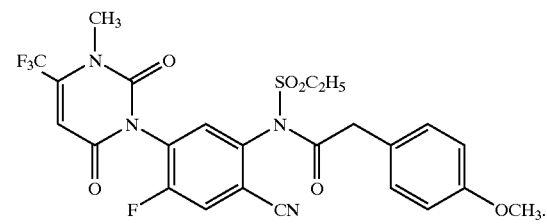

* * * * *